United States Patent
Dietrich et al.

(10) Patent No.: US 10,786,583 B2
(45) Date of Patent: Sep. 29, 2020

(54) PRE-SATURATION OF THE LIVER AND SUBSEQUENT ADMINISTRATION OF THE CONTRAST AGENT

(71) Applicant: B. Braun Melsungen AG, Melsungen (DE)

(72) Inventors: Thore Dietrich, Berlin (DE); Riad Bourayou, Berlin (DE); Eckart Fleck, Berlin (DE); Thorsten Keller, Berlin (DE); Jürgen Schmitt, Kirchhain (DE); Doris Röthlein, Kassel (DE)

(73) Assignee: B.Braun Melsungen AG, Melsungen (DE)

( * ) Notice: Subject to any disclaimer, the term of this patent is extended or adjusted under 35 U.S.C. 154(b) by 865 days.

(21) Appl. No.: 15/023,722

(22) PCT Filed: Sep. 25, 2014

(86) PCT No.: PCT/EP2014/070569
§ 371 (c)(1),
(2) Date: Mar. 22, 2016

(87) PCT Pub. No.: WO2015/044312
PCT Pub. Date: Apr. 2, 2015

(65) Prior Publication Data
US 2016/0228582 A1    Aug. 11, 2016

(30) Foreign Application Priority Data

Sep. 30, 2013 (EP) .................................... 13186703
May 22, 2014 (EP) .................................... 14169433

(51) Int. Cl.
*A61K 49/18* (2006.01)
*A61K 49/04* (2006.01)
*A61K 49/00* (2006.01)

(52) U.S. Cl.
CPC ...... *A61K 49/1806* (2013.01); *A61K 49/0021* (2013.01); *A61K 49/0076* (2013.01); *A61K 49/0471* (2013.01)

(58) Field of Classification Search
None
See application file for complete search history.

(56) References Cited

U.S. PATENT DOCUMENTS

| | | | | |
|---|---|---|---|---|
| 2008/0193372 A1* | 8/2008 | Lanza | ................. | A61K 9/1075 424/1.11 |
| 2008/0234389 A1* | 9/2008 | Mecozzi | ............. | A61K 9/0019 514/722 |
| 2008/0319315 A1* | 12/2008 | Kolodny | ........... | A61K 51/0491 600/431 |
| 2009/0280055 A1 | 11/2009 | Schrader et al. | | |

FOREIGN PATENT DOCUMENTS

| | | |
|---|---|---|
| CN | 101045042 A | 10/2007 |
| WO | WO 97/33563 A2 | 9/1997 |
| WO | WO 97/33563 A3 | 9/1997 |
| WO | WO 2008/153928 A2 | 12/2008 |

OTHER PUBLICATIONS

Abstract of European Patent—EP0670159, dated Sep. 6, 1995, 1 page.
"Medium-Chain Triglycerides," British Phamacopoeia vol. I & II, Monographs: Medicinal and Pharmaceutical Substances, Ph. Eur. Monograph 0868, 4 pages, Accessed online Feb. 29, 2016.
Yu et al., "A Versatile Reporter for Non-Invasive Physiology and Pharmacology Using Magnetic Resonance," Current Medicinal Chemistry, vol. 12, No. 7, 2005, pp. 819-848.
International Search Report for PCT/EP2014/070569 dated Dec. 16, 2014, 3 pages.

* cited by examiner

*Primary Examiner* — Jennifer Lamberski
(74) *Attorney, Agent, or Firm* — Dority & Manning, P.A.

(57) ABSTRACT

The present invention relates to an aqueous formulation for use in diagnostic detection wherein the aqueous formulation is administered prior to the administration of a fluorinated contrast agent or composition comprising a fluorinated contrast agent as well as to a method of administration. The invention further relates to the use of said aqueous formulation for the diagnostic detection of inflammatory pathological conditions using MR imaging. In addition the invention relates to a kit as well as a diagnostic kit suitable for use in diagnostic detection.

17 Claims, 9 Drawing Sheets

PRE-SATURATION OF THE LIVER AND SUBSEQUENT ADMINISTRATION OF THE CONTRAST AGENT

CROSS REFERENCE TO RELATED APPLICATIONS

This application is the national stage entry of International Patent Application No. PCT/EP2014/070569 having a filing date of Sep. 25, 2014, which claims priority to and the benefit of European Patent Application Nos. 13186703.8 filed in the European Patent Office on Sep. 30, 2013 and 14169433.1 filed in the European Patent Office on May 22, 2014, the entire contents of which are incorporated herein by reference.

The present invention relates to an aqueous formulation for use in diagnostic detection wherein the aqueous formulation is administered prior to the administration of a fluorinated contrast agent or composition comprising a fluorinated contrast agent as well as to a method of administration. The invention further relates to the use of said aqueous formulation for the diagnostic detection of inflammatory pathological conditions using MR imaging. In addition, the invention relates to a kit as well as a diagnostic kit suitable for use in diagnostic detection.

Inflammatory diseases are by far the most important causes of morbidity and mortality worldwide. While there are effective diagnostic and therapeutic methods for acute inflammatory diseases, predominately caused by pathogens, in many cases, the diagnosis of chronic inflammatory diseases is difficult and the treatment thereof is limited to symptomatic measures. Non-invasive imaging methods, such as echocardiography, computer tomography and nuclear magnetic resonance spectroscopy, provide detailed anatomic information and are thus valuable tools for evaluating the function of organs. However, with none of the methods mentioned has it been possible, to date, to unambiguously detect inflammatory processes with high spatial resolution.

EP 0670159 A1 discloses aqueous emulsions of oils that include a compound that carries a highly fluorinated alkyl group which, in turn, is connected to an alkane chain or a hydrogen atom.

WO 97/33563 discloses the use of fluorocarbons for the diagnosis and treatment of articular disorders. The fluorocarbons, which can be liquids, gels or emulsions, provide articular lubrification and cushioning which is effective in the treatment of e.g. osteoarthritis. In addition, the fluorocarbons may be used to provide high resolution articular images.

US 2009/0280055 A1 discloses the use of fluorocarbons such as perfluorooctyl bromide, perfluorooctane, perfluorodecalin or perfluoro-15-crown-5-ether for diagnostic purposes using imaging methods.

WO 2008/153928 A2 describes methods and compositions that lower the uptake of the radiopharmaceutical FDG, a glucose analog, by brown adipose tissue and the myocardium in FDG-PET/CT scans by orally administering a fatty nutrient several hours before the FGD. The FGD is present in the form of an aqueous solution.

DE 10 2007 015 598 discloses the use of fluorine compounds, such as perfluorooctylbromide, perfluorodecaline, perfluoro-15-crown-5-ether, in imaging processes whereby the fluorine compound is attached to a vehicle.

Most of the diagnostic agents used to date, for example gadolinium complexes used in visualization via MRI-techniques, cause serious side effects that may lead to severe damage of organs, especially the liver. Cases are known to the person skilled in the art where gadolinium complexes administered for diagnostic imaging led to the development of liver tumors.

Other diagnostic agents described in the prior art suffer from the drawback that they are radioactively labeled and thus not suitable for routine diagnostics. Further, the handling and preparation of such diagnostic agents is rather bothersome as severe constraints and restrictions have to be followed when using said diagnostic agents apart from being rather expensive. In addition, their use is restricted to special clinics that have PET equipment Aside from the mentioned drawbacks, some of the diagnostic agents using radioactive markers also show a poor contrast when applied in PET/CT scans. This is especially true for sugar analogs such as $^{18}$F-2-fluoro-2-deoxy-D-glucose (FDG), which are designed to accumulate in tissue which is pathologically characterized by an increased rate of metabolic activity in comparison to healthy tissue. However, certain types of cells such as brown adipose tissue and myocardium already show a high rate of activity, even in a healthy state. Consequently, the FDG, which is recognized by the organism as a source of sugar, will accumulate primarily in those regions of increased activity with the consequence that no differentiation between healthy and inflamed tissue can be made. In order to avoid natural accumulation it is necessary to directly influence the lipometabolism of the patient. This can be done by administering a fatty nutrient enterally prior to the administration of the radioactive labeled sugar. Due to the fact that two different metabolic pathways are addressed, i.e. the fat metabolism for the nutrient and the sugar metabolism for the diagnostic agent, formulation, administration and dosage have to be carefully adjusted and controlled, making the diagnostic procedure highly complicated and expensive, in addition to putting undue strain to the patient.

Although a number of fluorinated contrast agents are available for use in diagnostic detection via magnetic resonance imaging, and for which triggering of such serious side effects is not known, these contrast agents known in the prior art also suffer from several drawbacks, one of which being the rather high dosage of the contrast agent or contrast enhancing agent that has to be administered in order to achieve satisfactory imaging of inflamed tissue.

DESCRIPTION OF THE DRAWINGS

A full and enabling disclosure of the present invention, including the best mode thereof, directed to one of ordinary skill in the art, is set forth in the specification, which makes reference to the appended figures, in which.

Figure 1:
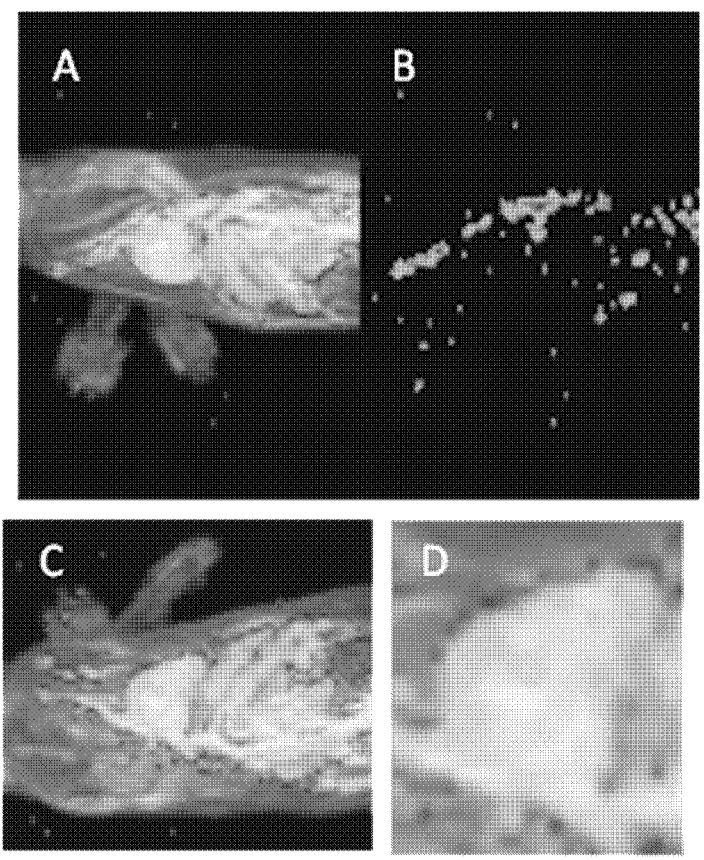
FIG. 1 shows reconstructions of the magnetic resonance imaging signals in the thorax of a rat.

It is an object of the present invention to provide a diagnostic agent that, although only administered in low dosages, delivers high contrast images when employed in diagnostic detection, for example in diagnostic detection via magnetic resonance imaging (MRI).

A further object of the present invention is the provision of a diagnostic agent that causes fewer side effects than the diagnostic agents presently used.

A first embodiment of the present invention is a phagocytosable-component-containing aqueous formulation (F), for use in diagnostic detection, wherein, prior to the administration of a fluorinated contrast agent or a composition comprising a fluorinated contrast agent, the aqueous formulation (F) is separately parenterally administered, preferably to a human or animal body.

Without being bound by theory it is believed that contrast agents as described in the present application are primarily phagocytized by cells associated with the immune system, such as monocytes and macrophages. However, it was surprisingly found that the contrast agent also accumulates in liver and spleen due to being phagocytized by Kupffer cells which are also part of the immune system. The withdrawal of the contrast agent by Kupffer cells from the blood stream, however, leads to a poor contrast in diagnostic imaging as only a small amount of the contrast agent accumulates in the inflamed tissue. It has surprisingly been found that the withdrawal can be minimized by saturating the liver and spleen by administering an oil-in-water emulsion prior to the administration of the contrast agent. This in turn leaves more of the contrast agent to accumulate in the inflamed tissue, improving the contrast and quality of diagnostic imaging.

Further, in contrast to the contrast agents and formulations described in the prior art, such as FDG or other fluorinated glucose derivatives, the fluorinated contrast agent according to the invention is generally not metabolized by the organism, thus avoiding possible harmful decomposition products.

Preferably, the aqueous formulation (F) according to the invention refers to a liquid formulation, for example in the form of an emulsion or a suspension. The aqueous formulation (F) is liquid at 20° C. The aqueous formulation (F) is pharmaceutically acceptable. Further preferably, the aqueous formulation (F) is intravenously administered, preferably to a mammal, especially a human.

Preferably, the phagocytosable component of aqueous formulation (F) according to the invention relates to a component which can be engulfed by macrophages. The aqueous formulation (F) is usually essentially free of contrast agents, in particular contrast agents which can be detected by MR techniques, especially fluorinated contrast agents. Within the meaning of the present invention essentially free of contrast agents means that the total amount of contrast agent(s) is less than 5 wt.-%, preferably less than 1.0 wt.-%, more preferably less than 0.1 wt.-% or less than 0.01 wt.-% or less than 0.001 wt.-%, especially preferred 0 wt.-%, based on the total weight of the aqueous formulation (F).

In an alternative aspect of the invention, the weight ratio of the fluorinated contrast agent to non-fluorinated contrast agents, especially non-fluorinated contrast agents possibly present in the aqueous formulation (F) is more than 0.1, preferably more than 1, more preferably more than 5, further preferably more than 10, further preferably more than 100 or more than 1000, especially more than 10000 or more than 1000000.

It is well known to the person skilled in the art that the visualization of inflammatory processes, especially of the cardiovascular system, is rather difficult. The majority of the contrast agents or contrast agent compositions that are employed for diagnostic detection of inflammatory processes are designed to accumulate in the inflamed areas which are distinguished by a high concentration of macrophages. Due to a naturally increased concentration of macrophages in the liver, relating to its function as a detoxifying organ, most of the administered contrast agent accumulates in the liver. Due to the close proximity of the liver to the cardiovascular system, visualization and detection of inflammatory processes of or in the heart is often ambiguous because of signal interference and low contrast, respectively.

It has surprisingly been found that saturation of the liver prior to the administration of a contrast agent or contrast agent composition enhances the contrast of images of inflammatory processes of the cardiovascular system.

Therefore, the aqueous formulation (F) which is administered first is a phagocytosable-component-containing aqueous formulation. The phagocytosable component saturates the liver in a manner that subsequently administered fluorinated contrast agents are detected in the liver in a significant lower amount. Phagocytosable components of the aqueous formulation (F) of the present invention are components which are engulfed by the macrophages of the liver. The phagocytosable compound is administered parenterally. Preferably the phagocytosable compound is pharmaceutically injectable.

The phagocytosable-component-containing aqueous formulation (F) is usually a dispersible system, preferably a colloidal system, especially an emulsion or suspension.

Preferably, the phagocytosable component of the present invention may be selected from non-fluorinated contrast agents, such as barium sulfate or iron oxide, and other components, such as dextrane particles, polymer particles or latex particles. In an especially preferred embodiment the phagocytosable component of the invention is in particular phagocytosable by Kupffer cells. Furthermore, the phargocytosable component can also be selected from droplets comprising/consisting of oils, especially plant oils or fish oil.

In a preferred embodiment the phagocytosable-component-containing aqueous formulation (F) is an aqueous emulsion (A), preferably an oil-in-water emulsion (A).

Therefore, a preferred embodiment of the present invention is a phagocytosable-component-containing aqueous formulation (F) for use in diagnostic detection, wherein the aqueous formulation (F) is an oil-in-water emulsion (A) which is administered in a first step and in a subsequent step a fluorinated contrast agent or a composition comprising a fluorinated contrast agent is administered.

The aqueous emulsion (A) is described in the following in more detail.

I) Emulsion (A)

It is assumed that the oil of emulsion (A) is taken up by the liver and blocks the macrophages therein. Thus, less contrast agent can accumulate in the liver and spleen. Therefore, the concentration of the contrast agent in the blood stream increases and more of the contrast agent is available to macrophages stemming from inflammatory processes and/or inflamed tissue, thus in turn, enhancing the contrast of the diagnostic detection.

The oil used in emulsion (A) according to the present invention should be biocompatible and present a low risk of health to the patient to whom it is administered. In an especially preferred embodiment the oil is pharmaceutically acceptable.

Accordingly, an embodiment of the present invention is preferred wherein the aqueous emulsion (A) comprises a triglyceride. In a further aspect of the invention emulsion (A) comprises a vegetable oil and/or a marine oil.

"Vegetable oil" refers to oil derived from plant seeds or nuts. Vegetable oils are typically "long-chain triglycerides" (LCTs), formed when three fatty acids (usually 14 to 22 carbons in length, with unsaturated bonds in varying numbers and locations, depending on the source of the oil) form ester bonds with the three hydroxyl groups of glycerol. In exemplary embodiments, vegetable oils of highly purified grade (also called "super refined") can be used to ensure safety and stability in emulsion (A). In preferred embodiments hydrogenated vegetable oils, which are produced by controlled hydrogenation of the vegetable oil, may be used.

The oil present in emulsion (A) is preferably chosen for its advantageous pharmacokinetic properties as well as in careful consideration of the risk to health it may present. Therefore, an embodiment of the present invention is preferred wherein the aqueous emulsion (A) comprises one or more oils selected from the group consisting of almond oil, babassu oil, blackcurrant-seed oil, borage oil, canola oil, caster oil, coconut oil, corn oil, cottonseed oil, olive oil, peanut oil, palm oil, palm-kernel oil, rapeseed oil, safflower oil, soybean oil, sunflower oil, sesame oil, medium-chain triglycerides (MCT), long-chain triglycerides (LCT) and fish oil.

"Medium chain triglycerides" (MCTs) are a class of triglyceride oil that can be either naturally derived or synthetic. MCTs are formed from fatty acids (FA) of 6 to 14 carbons, preferably 6 to 12 carbons, especially 8 to 10 carbons, in length. The MCT can contain caprylic acid (for example, in an amount of about 50% to about 80% by weight of the MCT), an 8-carbon saturated FA (8:0). The MCT can contain capric acid (for example, in an amount of about 20% to about 50% by weight of the MCT), a 10-carbon saturated FA (10:0). For example, the medium-chain triglycerides can contain triglycerides of caprylic acid and capric acid in an amount of at least 90% by weight of the medium-chain triglycerides. The description of the MCT for use in this disclosure can, for example, meet the requirements of EP monograph 0868, entitled "Triglycerides, Medium Chain" (Triglycerida saturate media) (EP 0868, 2008).

Apart from its biocompatibility, aqueous emulsion (A) should be of a form possessing properties that allow for an as patient-friendly as possible administration. Aqueous emulsion (A) should also exhibit pharmacokinetic properties that allow for rapid delivery of the oil to the liver and fast uptake therein. The best results have been achieved when the amount of oil present in aqueous emulsion (A) did not exceed the amount of water. An embodiment of the present invention is preferred wherein the aqueous emulsion (A) comprises an oil in an amount ranging from 5 to 40 wt.-%, preferably from 8 to 30 wt.-%, based on the total weight of aqueous emulsion (A).

As the patient already suffers from serious health issues, it is important to keep the imposition the diagnostic process presents to a minimum. Therefore, it is preferred that the uptake of the saturating agent, i.e. the phagocytosable-component-containing aqueous formulation (F), be as fast as possible. In order for formulation (F) to reach its destination quickly and without decomposition it is advantageous that phagocytosable-component-containing aqueous formulation (F) be transported via the blood stream.

Therefore, an embodiment of the phagocytosable-component-containing aqueous formulation (F) for use according to the invention is preferred wherein the aqueous formulation (F) is administered intravenously.

II) Fluorinated Contrast Agent or Composition Comprising a Fluorinated Contrast Agent The detection and localization of inflammatory processes, especially of the cardiovascular system, by non-invasive techniques are of utmost importance for the successful therapeutic treatment and cure of the affected patient. Contrast agents that are administered to the patient help to provide detailed images of the inflamed tissue. It has been found that the best results can be achieved when the contrast agent is fluorinated. Fluorinated contrast agents possess an enhanced bioavailability and target-specificity when employed in, for example, magnetic resonance imaging (MRI). The fluorinated contrast agents are taken up by monocytes/macrophages in such a way that the cells become specifically labeled.

Preferably, the fluorinated contrast agent is not metabolized by the organism of the human or animal body.

According to a further aspect of the invention, the fluorinated contrast agent is not a fluorinated glucose derivative, especially not FDG.

Preferably the fluorinated contrast agent is chosen to allow for the best image possible. At the same time the fluorinated contrast agent as well as the composition comprising the fluorinated contrast agent should be biocompatible and pose as low a risk to health as possible. In a preferred embodiment of the present invention the contrast agent is a fluorinated compound selected from the group consisting of partially fluorinated carbon compounds, perfluorinated carbon compounds, linear, cyclic or polycyclic fluorinated alkanes, bis(perfluoroalkyl)alkanes, perfluoroethers, perfluoroamines, perfluoroalkylbromide and perfluoroalkychloride.

A further preferred embodiment is a phagocytosable-component-containing aqueous formulation (F) for use according to the present invention wherein the fluorinated contrast agent is selected from the group consisting of a) semifluorinated compound of formula I:

$$CF_3-(CF_2)_x-(CH_2)_y-CH_3 \qquad (I)$$

wherein x is an integer ranging from 1 to 8 and y is an integer ranging from 2 to 10;

b) perfluorooctylbromide, c) perfluorodecylbromide,
d) perfluorooctane,
e) perfluorodecane and
f) perfluorodecalin.

Semifluorinated compounds within the meaning of the present invention are semifluorinated alkanes. The semifluorinated alkanes comprise a fluorocarbon and a hydrocarbon moiety. Commonly, semifluorinated alkanes follow the following nomenclatures: FXHY, wherein X represents the number of carbon atoms which are substituted by fluoro atoms and Y represents the number of carbon atoms which are substituted with hydrogen atoms. For example perfluorohexyloctane is represented by the formula: F6H8.

F6H8 is shown in the following formula:

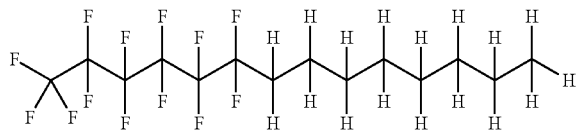 [SMILES: CCCCCCCCC(F)(F)C(F)(F)C(F)(F)C(F)(F)C(F)(F)C(F)(F)F]

Preferably, the fluorinated contrast agent is comprised in a contrast agent composition. In this way it is possible to improve and further enhance the properties necessary to achieve the best results with respect to the contrast of the diagnostic image and the biocompatibility and biokinetics of the fluorinated contrast agent and additionally, to ensure a satisfactory labeling of the macrophages by the contrast agent while simultaneously assuring high tolerance of the composition by the patient. With regard to tolerance by the patient, the transportation of the contrast agent in the body and the biocompatibility of the composition, an aqueous emulsion, henceforth referred to as emulsion (B), seems to be most suitable.

In a preferred embodiment of the invention the composition comprising the fluorinated contrast agent is an emulsion or a dispersion.

Further, it is preferred that the composition comprising the fluorinated contrast agent is an aqueous liquid composition wherein the fluorinated contrast agent is not dissolved or not completely dissolved in the aqueous phase. Preferably, the solubility of the fluorinated contrast agent in 1 liter water at 20° C. is less than 10 g, more preferably less than 2 g, especially less than 0.5 g, more especially less than 0.01 g, e.g. less than 0.001 g.

Therefore, a phagocytosable-component-containing aqueous formulation (F) for use according to the present invention is preferred wherein the composition comprising a fluorinated contrast agent is an aqueous emulsion (B) comprising
a) a fluorinated contrast agent, preferably a liquid fluorinated contrast agent, in particular a semifluorinated compound of formula I:

$$CF_3-(CF_2)_x-(CH_2)_y-CH_3 \quad (I)$$

wherein x is an integer ranging from 1 to 8 and y is an integer ranging from 2 to 10,
b) a medium-chain triglyceride (MCT) which is miscible with the semifluorinated compound at 20° C.; and
c) an emulsifier.

Semifluorinated compounds that are suitable for aqueous emulsion (B) of the present invention are reflected in formula (I):

$$CF_3-(CF_2)_x-(CH_2)_y-CH_3 \quad (I)$$

wherein x is an integer ranging from 1 to 8 and y is an integer ranging from 2 to 10.

In one embodiment, x in formula I ranges from 2 to 6, preferably from 3 to 6, more preferably from 4 to 6 and especially x is 5.

In a further preferred embodiment y in Formula (I) ranges from 2 to 9, preferably from 3 to 8, more preferably from 5 to 8, further preferably from 6 to 8 and especially y is 7.

Good results in terms of imaging and stability of emulsion (B) can be achieved with semifluorinated compounds of formula (I) wherein y is greater than x.

Especially preferred semifluorinated carbon compounds for use as fluorinated contrast agents in the present invention are perfluorohexyloctane (F6H8) and/or perfluorobutylpentane (F4H5).

Emulsion (B) further preferably comprises the semifluorinated compound together with a medium-chain triglyceride (MCT).

In a preferred embodiment, the triglyceride, preferably the MCT, is miscible with the semifluorinated compound at 20° C.

Within the meaning of the invention the triglyceride is miscible with the semifluorinated compound if, at a temperature of 20° C. and after mixing and subsequent storing at 20° C. for 24 hours, the triglyceride and the semifluorinated compound do not form separate continuous phases.

In a preferred embodiment, the triglyceride, especially the MCT, is miscible with the semifluorinated compound in any ratio. In particular, the semifluorinated compound and the triglyceride, especially the MCT, are miscible in a weight ratio of the semifluorinated compound to the MCT from 1:20 to 1:0.7, preferably 1:15 to 1:0.8, more preferably 1:10 to 1:0.9, further preferably 1:4 to 1:1, especially 1:2 to 1:1.

In a preferred embodiment of the invention the medium chain triglyceride (MCT) is glycerol which is esterified with carboxylic acids as specified in the following:
caproic acid in an amount of 2 wt.-% or less;
caprylic acid in an amount ranging from about 50 to about 80 wt.-%;
capric acid in an amount ranging from about 20 to about 50 wt.-%;
lauric acid in an amount of 3 wt.-% or less;
myristic acid in an amount of 1 wt.-% or less, wherein the weight-% (wt.-%) is based on the total weight of the fatty acids.

The medium-chain triglycerides (MCT) are excellent solvents for the semifluorinated compounds. In a preferred embodiment of the invention one or more MCTs can be used. MCT is commercially available as, for example, Miglyol 812 (SASOL GmbH Germany), or CRODAMOL GTCC-PN (Croda Inc, New Jersey).

According to an especially preferred embodiment of the present invention, aqueous emulsion (B) comprising the semifluorinated compound also comprises an MCT which consists of glycerol which is esterified with fatty acids comprising at least 50 wt.-% of fatty acids selected from the group of fatty acids having 7, 9 and 11 carbon atoms. Preferred may be triheptanoin.

III) Emulsifiers

For optimum administration, high target specificity and fast uptake it is important that the phagocytosable-component-containing aqueous formulation (F) for use according to the invention should be homogenous and not a two phase system having two or more continuous phases. The same consideration applies to the composition comprising a fluorinated contrast agent in the case that the composition is in the form of an emulsion.

Therefore, an embodiment of the phagocytosable-component-containing aqueous formulation (F) for use according to the invention is preferred wherein the aqueous formulation (F) is in the form of an aqueous emulsion (A) which further comprises an emulsifier, preferably selected from phospholipids.

Preferably, the composition comprising a fluorinated contrast agent also comprises an emulsifier, in the case the composition should be in form of an emulsion.

The emulsifier which may be present in the phagocytosable-component-containing aqueous formulation (F), preferably in the aqueous emulsion (A), as well as the emulsifier that may be comprised in the contrast agent composition may be identical or different compounds.

Suitable emulsifiers are described in detail below.

Preferably the emulsifiers are selected from phospholipids. Preferably, the emulsifiers are a phospholipid or a mixture of phospholipids.

In one aspect the emulsifiers may comprise lecithins, preferably naturally occurring lecithins such as soy lecithin, egg lecithin, sunflower oil lecithin, sphingosine, gangliosides, phytosphingosine, and combinations thereof. Hydrogenated lecithin, i.e. the product of controlled hydrogenation of lecithin, may also be additionally used in the emulsifiers.

Exemplary phospholipids useful in the present invention include, but are not limited to phosphatidyl choline, phosphatidylethanolamine, phosphatidylglycerol, phosphatidic acid, lyso-phosphtidylcholine and mixtures thereof. The phospholipid component of the compositions can be either a single phospholipid or a mixture of several phospholipids. The phospholipids employed may be natural or synthetic, but should be acceptable for medicinal application.

A non-exhaustive list of suitable phospholipids which may additionally be present in the emulsifiers is listed below:

Phosphatidic acids, including 1,2-Dimyristoyl-sn-glycero-3-phosphatidic acid, sodium salt (DMPA,Na), 1,2-Dipalmitoyl-sn-glycero-3-phosphatidic acid, sodium salt (DPPA,Na), 1,2-Distearoyl-sn-glycero-3-phosphatidic acid, sodium salt (DSPA,Na); phosphocholines, including 1,2-Dilauroyl-sn-glycero-3-phosphocholine (DLPC), 1,2-Dimyristoyl-sn-glycero-3-phosphocholine (DMPC), 1,2-Dipalmitoyl-sn-glycero-3-phosphocholine (DPPC), 1,2-Distearoyl-sn-glycero-3-phosphocholine (DSPC); phosphoethanolamines, including 1,2-Dilauroyl-sn-glycero-3-phosphoethanolamine (DLPE), 1,2-Dimyristoyl-sn-glycero-3-phosphoethanolamine (DMPE), 1,2-Dipalmitoyl-sn-glycero-3-phosphoethanolamine (DPPE), 1,2-Distearoyl-sn-glycero-3-phosphoethanolamine (DSPE); phosphoglycerols, including 1,2-Dilauroyl-sn-glycero-3-phosphoglycerol, sodium salt (DLPG, Na), 1,2-Dimyristoyl-sn-glycero-3-phosphoglycerol, sodium salt (DMPG, Na), 1,2-Dimyristoyl-sn-glycero-3-phospho-sn-1-glycerol, ammonium salt (DMP-sn-1-G,NH4), 1,2-Dipalmitoyl-sn-glycero-3-phosphoglycerol, sodium salt (DPPG,Na), 1,2-Distearoyl-sn-glycero-3-phosphoglycerol, sodium salt (DSPG,Na), 1,2-Distearoyl-sn-glycero-3-phospho-sn-1-glycerol, sodium salt (DSP-sn-1G,Na); phosphoserines, including 1,2-Dipalmitoyl-sn-glycero-3-phospho-L-serine, sodium salt (DPPS,Na); mixed chain phospholipids, including 1-Palmitoyl-2-oleoyl-sn-glycero-3-phosphocholine (POPC), 1-Palmitoyl-2-oleoyl-sn-glycero-3-phosphoglycerol, sodium salt (POPG,Na), 1-Palmitoyl-2-oleoyl-sn-glycero-3-phosphoglycerol, ammonium salt (POPG,NH4); lysophospholipids, including 1-Palmitoyl-2-lyso-sn-glycero-3-phosphocholine (P-lyso-PC), 1-Stearoyl-2-lyso-sn-glycero-3-phosphocholine (S-lyso-PC); pegylated phospholipids, including N-(Carbonyl-methoxypolyethyleneglycol 2000)-MPEG-2000-DPPE, sodium salt, N-(Carbonyl-methoxypolyethyleneglycol 5000)-MPEG-5000-DSPE, sodium salt, N-(Carbonyl-methoxypolyethyleneglycol 5000)-MPEG-5000-DPPE, sodium salt, N-(Carbonyl-methoxypolyethyleneglycol 750)-MPEG-750-DSPE, sodium salt, N-(Carbonyl-methoxypolyethyleneglycol 2000)-MPEG-2000-DSPE, sodium salt.

In a preferred embodiment, the emulsifiers comprise egg lecithin comprising 60-80% wt/wt, such as 67% wt/wt phosphatidyl choline; 10-20% wt/wt, such as 15% wt/wt, phospatidylethanolamine; <=3% wt/wt, such as 2% wt/wt, sphingomyelin; and <=3% wt/wt, such as 1% wt/wt, lysophosphatidylcholine.

"Egg lecithin PL90" (Fresenius Kabi AB) is one example of an egg lecithin having such a phospholipid content.

In particular, good results can be achieved with emulsifiers comprising a lecithin comprising about 80 to about 85 wt.-% phosphatidylcholine;
about 7.0 to about 9.5 wt.-% phosphatidylethanolamine;
less than 3 wt.-% lysophosphatidylcholine;
less than 0.5 wt.-% lysophosphatidylethanolamine; and
about 2 to about 3 wt.-% sphingomyelin.

In a preferred embodiment, aqueous emulsion (A) comprises an emulsifier in an amount ranging from 0.5 wt.-% to 5.0 wt.-% wherein the wt.-% are based on the total weight of emulsion (A). The best results have been achieved when the emulsifier was present in an amount ranging from 0.5 wt.-% to 2 wt.-%, preferably from 1.0 wt.-% to 1.5 wt.-% wherein the wt.-% are based on the total weight of emulsion (A).

In case the composition comprising a fluorinated contrast agent is present in the form of an emulsion and contains an emulsifier, it is preferred that the emulsifier comprises a mixture of phospholipids and glycolipids.

Glycolipids are lipids with a carbohydrate attached. Glycolipids are phosphorus-free membrane lipids of cell membranes wherein one or more mono- or oligosaccharides are connected to a lipid. The lipids are fatty acids which are connected via ester bonds to glycerol or via amide bonds to sphingosin.

In a preferred embodiment, the composition comprising a fluorinated contrast agent additionally comprises glycolipids, which are preferably selected from glyceroglycolipids, such as mono galactosyldiglyceride or glycosphingolipids or cerebrosides.

In a preferred embodiment, the amount of glycolipids is 5 to 30 wt.-%, preferably 10 to 28 wt.-% based on the total weight of the sum of glycolipid and phospholipid. Mixtures of phospholipids and glycolipids are commercially available as Lipoid S 75 ex Lipoid GmbH, Germany.

In an especially preferred embodiment the emulsifier comprises
about 68 to about 73 wt.-% phosphatidylcholine;
about 7 to about 10 wt.-% phosphatidylethanolamine;
less than about 3 wt.-% lysophosphatidylcholine; and
about 14 to about 25 wt.-% glycolipids, wherein all weight are based on the total amount of sum of glycolipids and phospholipids.

Emulsion (B) preferably comprises 0.5 to 5 wt.-%, more preferably 1.0 to 4.0 wt.-% of an emulsifier wherein the amount is based on the total weight of emulsion (B).

In a preferred embodiment, the fluorinated contrast agent or the composition comprising a fluorinated contrast agent is administered subsequently to the administration of the phagocytosable-component-containing aqueous formulation (F). Preferably the fluorinated contrast agent or the composition comprising a fluorinated contrast agent is administered in a way that keeps the administration process as simple and patient-friendly as possible. Therefore, an embodiment is preferred wherein the fluorinated contrast agent or the composition comprising a fluorinated contrast agent is administered parenterally.

The phagocytosable-component-containing aqueous formulation (F) of the invention usually does not comprise any form of contrast agent. Preferably, the weight ratio of the amount of contrast agent present in formulation (F), if present at all, to the amount of contrast agent present in the composition comprising the contrast agent is less than 1:4, preferably less than 1:10, more preferably less than 1:100 or less than 1:500 or less than 1:1000.

In a preferred embodiment, the phagocytosable-component-containing aqueous formulation (F) is essentially free of contrast agents. Essentially free within this meaning means that the formulation (F) comprises less than 5 wt.-%, preferably less than 1 wt.-%, more preferably less than 0.1 wt.-%, especially less than 0.001 wt.-% or 0 wt.-% contrast agent, wherein the amount is based on the total weight of the formulation (F).

A further embodiment of the invention is a fluorinated contrast agent or a composition comprising a fluorinated contrast agent for use in the diagnostic detection, wherein, prior to the administration of said fluorinated contrast agent or said composition comprising a fluorinated contrast agent, an phagocytosable-component-containing aqueous formulation (F) is separately administered.

IV) Phagocytosable-Component-Containing Aqueous Formulation (F) and the Fluorinated Contrast Agent for Use in Diagnostic Imaging Non-invasive diagnostic techniques are of utmost importance for the detection and diagnostic treatment of inflammatory processes of the body as they provide a fast and efficient form of diagnostics that is distinguished by its low imposition on the patient and fast recovery should the patient suffer from any side effects.

Therefore, in a preferred embodiment of the present invention the phagocytosable-component-containing aqueous formulation (F) for use according to the present invention is used in the diagnostic detection of inflammatory processes by means of an imaging procedure.

Preferably, the non-invasive imaging procedure is a magnetic resonance (MR) imaging procedure.

As described above, the generation of images suitable for diagnostic detection of inflammatory processes, especially those of the cardiovascular system, is often rather challenging since most of the contrast agent accumulates in the liver and spleen. Therefore, the amount of contrast agent available for labeling of the macrophages in the inflamed tissue is significantly reduced. Additionally, due to high concentrations of contrast agent in the liver and the physical proximity of the liver to the heart, images taken of the cardiovascular system are often of poor contrast, thus rendering the analysis of the images and the diagnosis more onerous.

It has surprisingly been found that the administration of a phagocytosable-component-containing aqueous formulation (F), especially an oil-in-water emulsion (A), prior to the administration of a fluorinated contrast agent or a composition comprising a fluorinated contrast agent leads to an enhanced contrast of the generated images, thus significantly improving not only the quality of the diagnostic methods but also the development of an optimal treatment.

Therefore, a further embodiment of the invention is a phagocytosable-component-containing aqueous formulation (F) for use according to the invention for use in the diagnostic detection of inflammatory processes by means of an imaging procedure wherein the formulation (F) is an oil-in-water emulsion (A) comprising
i) 5 to 40 wt.-% of an oil selected from triglyceride,
ii) 0.5 to 5 wt.-% of an emulsifier, preferably a phospholipid,
iii) optionally 0.1 to 5 wt.-% of a tonicity agent, and
iv) 55 to 93 wt.-% water, wherein the wt.-% are based on the total weight of the oil-in-water emulsion (A), which is administered in a first step and in a subsequent step preferably a composition, comprising a fluorinated contrast agent, in the form of an aqueous emulsion (B) comprising
i) 1 to 20 wt.-% of a semifluorinated compound of formula I:

$$CF_3-(CF_2)_x-(CH_2)_y-CH_3 \qquad (I)$$

wherein x is an integer ranging from 1 to 8 and y is an integer ranging from 2 to 10,
ii) 1 to 20 wt.-% of a triglyceride which is miscible with the semifluorinated compound, preferably medium-chain triglyceride (MCT); and
iii) 0.1 to 5 wt.-% of an emulsifier, is administered, wherein the wt.-% are based on the total weight of emulsion (B) is administered.

In a preferred embodiment of the invention, aqueous emulsion (B) also comprises water in an amount ranging from 70 to 98 wt.-%, preferably 70 to 90 wt.-%, based on the total weight of emulsion (B).

V) Additional Components

In a preferred embodiment of the present invention the phagocytosable-component-containing aqueous formulation (F), preferably the oil-in water emulsion (A), may further comprise additional components, for example to adjust the pharmacokinetic and biocompatibility, especially if the formulation (F) is an oil-in-water emulsion (A). The same applies for the composition comprising a fluorinated contrast agent, especially if the composition is in form of an emulsion (B).

It is to be understood, that the expression "emulsions" refers to both emulsion (A) and emulsion (B), if not stated otherwise.

The additional components as well as their amount may differ according to the respective emulsion.

In some embodiments, the aqueous emulsions may optionally comprise a co-surfactant. Exemplary co-surfactants include, but are not limited to, cholesterol, oleic acid, oleate, Tween80 (PEG-sorbitan monooleate), HCO-60, Solutol H15 (polyoxyethylene-660-hydroxystearate), PEG-400 (polyethylene glycol), Pluronic F68 (BASF), Cremophor EL (polyoxyethylene-35-ricinoleate), or the salt of a bile acid, such as deoxycholic acid. In other embodiments the co-surfactant is selected from the group consisting of $C_{12-22}$ fatty acids, salts thereof and/or mixtures thereof, such as from $C_{16-20}$ fatty acids, salts thereof and/or mixtures thereof, or from $C_{18}$ fatty acids, salts thereof and/or mixtures thereof. In specific embodiments, the fatty acid is monounsaturated.

In some embodiments, the co-surfactant may be present in the emulsions in an amount (wt.-%) greater than or equal to 0.005%, greater than or equal to 0.01%, or greater than or equal to 0.02%. In accordance with any of these embodiments the co-surfactant may be present in an amount (wt.-%) less than or equal to 4%, less than or equal to 1%, or less than or equal to 0.04%, based on the total weight of the respective emulsion.

In specific embodiments, the co-surfactant is selected from the group consisting of long-chain fatty acids, such as palmitic acid, oleic acid or stearic acid, or the alkali salts thereof. Oleate and/or oleic acid, particularly sodium oleate, are particularly suitable co-surfactants.

In certain embodiments where the co-surfactant is oleate and/or oleic acid, the co-surfactant may be present in an amount (wt.-%) equal to or greater than 0.005 wt.-%, equal to or greater than 0.01 wt.-%, or equal to or greater than 0.02 wt.-%. In accordance with any of these embodiments, the co-surfactant may be present in an amount (wt.-%) less than or equal to 0.5 wt.-%, less than or equal to 0.2 wt.-%, less than or equal to 0.1 wt.-%, or less than or equal to 0.05 wt.-%. In specific embodiments, the co-surfactant is sodium oleate and is present in an amount of 0.03 wt.-% (0.3 g/l). The emulsions described herein may be suitable for parenteral infusion, such as intravenous infusion. In specific embodiments, the concentration of certain co-surfactants therefore is kept to a minimum to prevent side effects such as irritation, cytochrome P450 inhibition, etc. In specific embodiments, Pluronic F68 (poly(ethyleneglycol)-13-poly(propylene glycol co-propylene glycol) is present in an amount less than 0.7 wt.-%, or less than 0.5 wt.-%. In other specific embodiments, Solutol-HS (Macrogol-15-hydroxystearate) is present in an amount less than 1.2 wt.-%, or less than 1 wt.-%.

It is to be understood that the amounts (wt.-%) given are based on the total weight of the respective emulsion in which the respective component is present.

The co-surfactants used may differ from each other, depending on the respective emulsion.

The emulsions according to the invention may further comprise a tonicity agent. Such compositions may have an osmolality in the range of 200-1000 mOsm/kg, preferably 220 to 800 mOsm/kg, especially 250 to 600 mOsm/kg.

In accordance with specific embodiments of the invention, the emulsions may be isotonic and iso-osmotic. The emulsions may have an osmolality of 220-600 mOsm/kg, or 230-360 mOsm/kg.

Suitable tonicity agents include potassium or sodium chloride, trehalose, sucrose, sorbitol, glycerol, glucose, xylitol, mannitol, polyethylene glycol, propylene glycol, albumin, amino acids and mixtures thereof. In certain embodiments, an osmolality of 270 to 330 mOsm/kg, such as 280 to 300 mOsm/kg, is achieved with an agent that also increases osmotic pressure, such as glycerol, dextrose, lactose, sorbitol or sucrose.

In one embodiment, the tonicity agent is a physiologically tolerated polyol, such as glycerol, sorbitol or xylitol. In a specific embodiment, the tonicity agent is glycerol.

The tonicity agent may be present in an amount ranging from 0.1 to 10 wt.-%, preferably 0.5 to 8 wt.-%, more preferably 1 to 5 wt.-%, based on the total weight of the respective emulsion.

The tonicity agent is generally used in an amount that does not have adverse biological effects, but is sufficient to provide iso-osmotic and/or isotonic compositions. When glycerol is the osmotic agent, glycerol may be present in the range of 2 to 5% (wt.-%), such as 2.1% to 2.9% (wt.-%), including 2.3% to 2.7%. In specific embodiments, the emulsions of the present invention comprise 2.5% glycerol (25 g/l). In a further embodiment, the tonicity agent is present in an amount of 2.5 wt.-% or more, based on the total weight of the respective emulsion.

In some embodiments, the emulsions according to the present invention have a pH within the range of pH 6.0 to pH 10.0, such as pH 6.5 to pH 9.0, including pH 7.5 to 8.5. The pH may be adjusted by methods known in the art, e.g., through the use of an appropriate base that neutralizes the negative charge on the fatty acids, through the use of an appropriate buffer, or a combination thereof. A variety of bases and buffers are suitable for use with the emulsions of the present invention. One skilled in the art will appreciate that the addition of buffer to the emulsions will affect not only the final pH, but also the ionic strength of the emulsions. High ionic strength buffers may negatively impact the zeta potential of the emulsions and are, therefore, not desirable.

In a preferred embodiment, aqueous emulsion (A) and aqueous emulsion (B) may have the same or different pH values.

In a preferred embodiment sodium hydroxide and hydrochloric acid are used to adjust the pH value of the emulsions, respectively.

In order to further stabilize the emulsions of the invention, i.e. aqueous emulsion (A) and aqueous emulsion (B), against oxidative processes an antioxidant may be present. In a preferred embodiment, the emulsions additionally comprise an antioxidant, preferably alpha-tocopherol.

The emulsions according to the present invention optionally comprise one or more pharmaceutically acceptable additives, such as acidifying, alkalizing, binding, chelating, complexing or solubilising agents, antiseptics, preservatives (including antimicrobials and antioxidants), suspending agents, stabilizing agents, wetting agents, viscosity modifying agents, solvents, cryo-protectants, diluents, lubricants and other biocompatible materials or therapeutic agents. In certain embodiments, such additives assist in further stabilizing the emulsions or in rendering the emulsions of the present invention biocompatible.

According to a preferred embodiment of the present invention, the additives present in aqueous emulsion (A) and aqueous emulsion (B) may differ in structure as well as in the amount present in the respective emulsion.

It has been found that good diagnostic results can be achieved with emulsions having an oil droplet size in the nano range. According to a preferred aspect of the invention, the particles of the discontinuous phase, i.e. the oily phase, have an average particle diameter preferably ranging from 1 to 500 nm, more preferably ranging from 50 to 450 nm and further preferably ranging from 100 to 400 nm, as measured through photon correlation spectroscopy (PCS) at 25° C.

VI) Diagnostic Imaging

It has been found that the administration of an phagocytosable-component-containing aqueous formulation (F), preferably an oil-in-water emulsion (A) according to the present invention, prior to the administration of the fluorinated contrast agent or the composition comprising a fluorinated contrast agent leads to a saturation of the liver. This, in turn, enhances the contrast of images of the surrounding organs, especially the cardiovascular system, as more of the contrast agent is present in the blood stream to attach to the macrophages which are present in the inflamed tissue. In addition, due to the higher amount of contrast agent available in the blood stream, not only the time required to achieve a satisfactory image of the inflamed area is significantly shortened but also the extend of the inflammatory process, e.g. after a cardiac infarction, can be determined in much more detail.

Preferably the phagocytosable-component-containing aqueous formulation (F) for use according to the present invention is for use as contrast enhancing agent for diagnostic detection by means of an imaging procedure, in particular where the imaging process is based on measuring the nuclear magnetic resonance of the $^{19}$F isotope of the fluorinated contrast agent, preferably a semifluorinated compound.

The evaluation of the corresponding measurements and conversion thereof into an image is known to the skilled person, as can be seen, for example, from:

Haacke M E, Brown W R, Thompson M R, Venkasetan R: Magnetic Resonance Imaging-Physical Principles and Sequence Design, Wiley, New York, 1999;

Yu J X, Kodibagkar V D, Cui W, Mason R P. 19F: a versatile reporter for non-invasive physiology and pharmacology using magnetic resonance; Curr Med Chem. 12: 819-48, 2005;

Wernick M N, Aarsvold J N Emission Tomography: The Fundamentals of PET and SPECT, Academic Press, London, 2004.

The phagocytosable-component-containing aqueous formulation (F) and/or the fluorinated compound of the invention or the composition comprising the fluorinated compound of the invention is particularly suitable to detect inflammatory processes. Therefore, according to a preferred embodiment of the invention, the aqueous formulation (F) and/or the fluorinated compound of the invention or the composition comprising the fluorinated compound is for the diagnostic detection, by means of an imaging procedure, of inflammatory processes selected from the group consisting of inflammatory reactions peripheral to infarctions such as myocardial infarction, stroke; inflammation of organs, such as myocarditis, encephalitis, meningitis; multiple sclerosis; inflammation of the gastrointestinal tract, such as Crohn's disease; inflammation of the vessels, such as arteriosclerosis, in particular vulnerable plaques; detection of abscesses and also arthritis, wherein the imaging process is based on measuring the nuclear magnetic resonance of the $^{19}$F isotope.

In a further preferred embodiment of the invention, the aqueous phagocytosable-component-containing aqueous formulation (F) and/or the fluorinated compound of the invention or the composition comprising the fluorinated compound is for diagnostic detection, based on non-invasive imaging procedures of the cardio vascular system, including the myocardium, arteries and veins; inflammatory reactions occurring in disease processes like myocardial infarction, myocarditis, atherosclerosis and thrombosis leading to inflammatory and degenerative processes of the vasculature found in neurology such as stroke or tumor; pulmology such as thrombosis, inflammation, sarcoidosis; gastroenterology such as tumour, inflammatory bowel diseases such as Crohn's disease; and rheumatology such as autoimmune diseases of the vessels such as Takayasu arteritis.

A further embodiment of the invention refers to a method comprising procedures for acquiring non-invasive imaging of a patient to whom, in a first step, a phagocytosable-component-containing aqueous formulation (F) and, in a subsequent step, a fluorinated contrast agent or a composition comprising a fluorinated contrast agent is administered.

Preferably, the time difference between the administration of the phagocytosable-component-containing aqueous formulation (F) and the administration of the fluorinated contrast agent or the composition comprising a fluorinated contrast agent is chosen in a way that allows for the concentration of the saturating agent, for example the oil in an oil-in-water emulsion (A), to reach a level such that the majority of the macrophages in the liver are blocked and the liver is saturated. As is obvious to the person skilled in the art, the time difference depends on the biokinetic properties of the phagocytosable-component-containing aqueous formulation (F), meaning the method of transportation and the uptake in the liver. Therefore, the time difference should not be too short since the saturating agent has to be able to reach its destination. On the other hand, the time frame in which the fluorinated contrast agent or the composition comprising a fluorinated contrast agent is administered should not be too long so as to prevent the decomposition of the saturating agent by the liver before the fluorinated contrast agent has accumulated in the inflamed tissue.

An embodiment of the method of the invention is preferred wherein the time difference between the first step and the subsequent step is at least 15 seconds, preferably at least 30 seconds, especially ranging from 1 minute to 10 hours, for example from 5 minutes to 1 hour. Usually the time between the first administration with the phagocytosable-component-containing aqueous formulation (F) and the second administration with the fluorinated contrast agent or the composition comprising the fluorinated contrast agent should be sufficient to saturate the macrophages of the liver, in particular at least about 20%, more preferably at least about 40% or at least about 60%, especially at least about 80 or at least about 90% of the macrophages of the liver should be saturated. In particular, the saturation of the liver should be such that a clear and non-ambiguous image of the surrounding organs, especially the cardiovascular system can be achieved.

Several methods of visualization may be employed in the present invention, for example magnetic resonance technique (MRT), computer tomography (CT), optical imaging, ultra sound, positron emission tomography (PET), single-photon emission computed tomography (SPECT) or optical coherence tomography (OCT). Preferably the method of visualization is non-invasive.

In a preferred embodiment, the non-invasive imaging procedure is a magnetic resonance (MR) imaging procedure.

In a further preferred embodiment of the method of the invention, the imaging process is based on measuring the nuclear magnetic resonance of the $^{19}$F isotope or of the $^{19}$F isotope and the $^1$H isotope.

The presence of $^{19}$F and/or $^{18}$F isotopes in the fluorinated contrast agents allows the advantage of using devices known in the prior art, namely magnetic nuclear resonance spectroscopy with $^{19}$F isotopes and/or the use of positron emission spectroscopy of $^{18}$F isotopes. Further, a native image, i.e. an image without contrast agent, can be taken of the inflamed tissue, e.g. by measuring the nuclear magnetic resonance of the $^1$H isotope, even after the fluorinated contrast agent has been administered, without interference of the fluorinated contrast agent, leading to a more efficient diagnostic system in a shorter amount of time.

By the use of the phagocytosable-component-containing aqueous formulation (F) according to the invention the following pathological conditions can especially be detected:

1) Visualization of lymph nodes and their pathological enlargement
   a) cancers that directly affect the lymph nodes: Hodgkin's disease, non-Hodgkin lymphomas;
   b) tumor metastases, for example, from breast cancer;
   c) viral and bacterial infections, for example, syphilis, tuberculosis;
2) Inflammation reactions in the border zone of
   a) infarctions, for example, myocardial infarction, stroke;
   b) tumors;
3) inflammation of organs: myocarditis, encephalitis, meningitis (cerebral and spinal meninges);
4) multiple sclerosis;

5) inflammations of the gastrointestinal tract, for example, Crohn's disease;
6) inflammation of the vessels, for example, arteriosclerosis, especially so-called "vulnerable plaques";
7) detection of abscesses;
8) detection of arthritis.

VII) Kit

The diagnostic treatment of a patient suffering from inflammatory conditions should be a gentle process that presents the least strain possible to the already weakened patient. Apart from using non-invasive detection techniques and providing contrast agents and contrast agent compositions that preferably cause no negative side effects, another aspect of a patient-friendly treatment is the time that is needed for the diagnostic procedures. The diagnosis should be reached as fast as possible to minimize both psychological and physiological strain. Preferably, tedious mixing of the components should be avoided, on the one hand to save time and on the other hand to avoid potential hazards to both the patient and staff that may be caused by false handling of the components.

Therefore, a further object of the present invention is a kit comprising
a) a container comprising a phagocytosable-component-containing aqueous formulation (F) as defined above and
b) a container comprising a fluorinated contrast agent or a composition comprising a fluorinated contrast agent as defined above.

The material of the container is preferably inert and does not react with the contents. Further preferred is a material that additionally protects the contents of the containers against exposure that may result in the decomposition of the contents, e.g. heat and/or light. Preferably, the material is selected from the group consisting of glass and organic polymers and mixtures thereof. Preferred organic polymers are polyethylene and/or polypropylene.

Preferably the container can be sealed to avoid contamination of the contents by, for example bacteria.

In a preferred embodiment of the kit, the containers are arranged in such a way to prevent unintentional mixing of the contents.

In a preferred embodiment the phagocytosable-component-containing aqueous formulation (F) is an aqueous oil-in-water emulsion (A) as described above.

Further preferred is an embodiment, in which the aqueous formulation (F) is an oil-in-water emulsion (A) and the fluorinated contrast agent or the composition comprising a fluorinated contrast agent is an emulsion (B).

Therefore, in a preferred embodiment the kit comprises
a) a container comprising aqueous emulsion (A) and
b) a container comprising aqueous emulsion (B).

Preferably, the kit consists of one container which is divided into two compartments that are, for example, separated by a layer of glass or organic polymer. Preferably, one container comprises the phagocytosable-component-containing aqueous formulation (F) and the other container comprises the fluorinated contrast agent or the composition comprising a fluorinated contrast agent.

In an alternative preferred embodiment, the kit consists of two containers which are separate or the containers can be separated without breaking so as to allow separate storage of the containers which is adjusted to the requirements of the contents.

A preferred embodiment is a kit according to the invention for use in the diagnostic detection of inflammatory processes.

A further object of the present invention is a diagnostic kit comprising
a) a container comprising a phagocytosable-component-containing aqueous formulation (F) and
b) a container comprising a fluorinated contrast agent or a composition comprising a fluorinated contrast agent.

In a preferred embodiment the phagocytosable-component-containing aqueous formulation (F) comprised in the diagnostic kit according to the invention is an oil-in-water emulsion (A), as described in the invention. The fluorinated contrast agent or the composition comprising a fluorinated contrast agent is preferably an emulsion (B) as described in the invention. Preferably the diagnostic kit according to the invention is used in the diagnostic visualization of inflammatory processes.

In the following, the invention is further illustrated by way of examples.

The test animal, a rat, was anaesthetized with a mixture of Domitor® and Dormicum®V 5 g/5 ml. Domitor® belongs to the class of alpha-2 adrenergetic agonists and is available from Pfizer. Dormicum®V 5 g/5 ml belongs to the class of benzodiazepines and is available from Roche Pharma AG. After the rat was narcotized, a long-stay venous catheter was placed in the tail vein of the rat. 2 ml of aqueous emulsion (A) were administered via the venous catheter. The content of aqueous emulsion (A) is shown in Table 1. After six minutes, 1.5 ml of an aqueous emulsion (B) was injected as contrast agent, the composition of which is reflected in Table 2. The test animal was then imaged using MRI-technique.

TABLE 1

| Oil in water emulsion (A) | |
| --- | --- |
| Component | Amount (% w/V) |
| soy bean oil[1] | 10 |
| MCT | 10 |
| egg lecithin[2] | 1.2 |
| glycerol | 2.5 |
| all-rac-α-tocopherol | 0.017 ± 0.004 |
| sodium oleate | 0.03 |
| water for injection (WFI) | ad 100 |

[1] = LCT = long chain triglyceride
[2] = Lipoid E 80, ex Lipoid GmbH, Germany

TABLE 2

| Aqueous emulsion (B) containing the fluorinated contrast agent | |
| --- | --- |
| Component | Amount (% w/V) |
| F6H8 | 8 |
| MCT | 12 |
| Lipoid S 75[3] | 2 |
| a-tocopherol | 0.02 |
| glycerol | 2.5 |
| sodium oleate | 0.03 |
| NaOH | Ad pH 8.2 |
| water for injection (WFI) | Ad 100 |

[3]Phospholipid ex Lipoid GmbH, Germany (soya phospholipid with 14 to 25 wt.-% glycolipid)

The MCT used in Table 1 and Table 2 has a fatty acid composition as shown in Table 3 wherein the weight-% are based on the total amount of fatty acid.

TABLE 3

Suitable MCT Compositions

| Fatty Acid | chemical formula | Amount (wt.-%) |
|---|---|---|
| caproic acid | $C_6H_{12}O_2$ | ≤2.0% |
| caprylic acid | $C_8H_{16}O_2$ | 50.0-80.0% |
| capric acid | $C_{10}H_{20}O_2$ | 20.0-50.0% |
| lauric acid | $C_{12}H_{24}O_2$ | ≤3.0% |
| myristic acid | $C_{14}H_{28}O_2$ | ≤1.0% |

In order to check whether the emulsions according to the invention can be visualized in vivo by means of MRI and detected in the target tissue, pharmacokinetic examinations were first performed.

FIG. 1 shows reconstructions of the magnetic resonance imaging signals in the thorax of a rat. The acquisition was taken after an aqueous emulsion (B) (as described in Table 2) was administered. The accumulation of the emulsion in the blood pool of the heart (the target tissue) is shown. Exemplary 3D reconstructions of the anatomic T2 TSE and the colored 3D $^{19}F$ sequences have been merged in a single data set (image A). Image B shows the same data set wherein the liver has been removed by post-processing. In the row below, a different view of the merged 3D data set (image C) and an enlarged view of the heart (image D) are shown.

Thus, it can be shown that the contrast agent described in the invention can be visualized in vivo in the myocardium. Further, the representation of an infarction in MRI was examined. The results are shown in the following FIG. 2.

Figure 2:
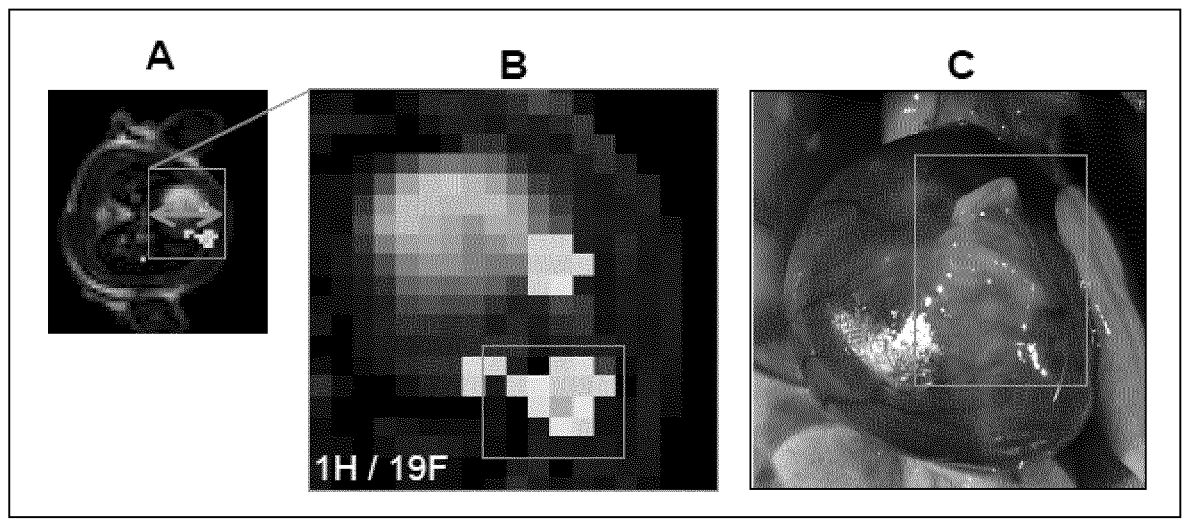
FIG. 2 shows an infarction in the heart of a rat via magnetic resonance imaging.

FIG. 2 shows: (Image A) Rat thorax in transversal section in the myocardial area in vivo in a T2-weighted MRI image (1.5 Tesla, Philips), which is superimposed with the colored $^{19}F$ image ($^1H/^{19}F$), with the same geometry 24 h after application of the aqueous emulsion (B) comprising the fluorinated contrast agent in accordance with Table 2. (Image B) The myocardium as a detail of the $^1H/^{19}F$ image, showing the enrichment of the fluorinated contrast agent in the area of the myocardial infarction and of the site of adhesion between the pericardium and the ribs caused by the surgery. (Image C) In situ recording of rat heart, which shows a strongly pronounced inflammation of the pericardium (gray outline) beside the infarcted area.

Thus, it could be shown that the fluorinated contrast agent becomes enriched in the infarcted area.

Figure 3:
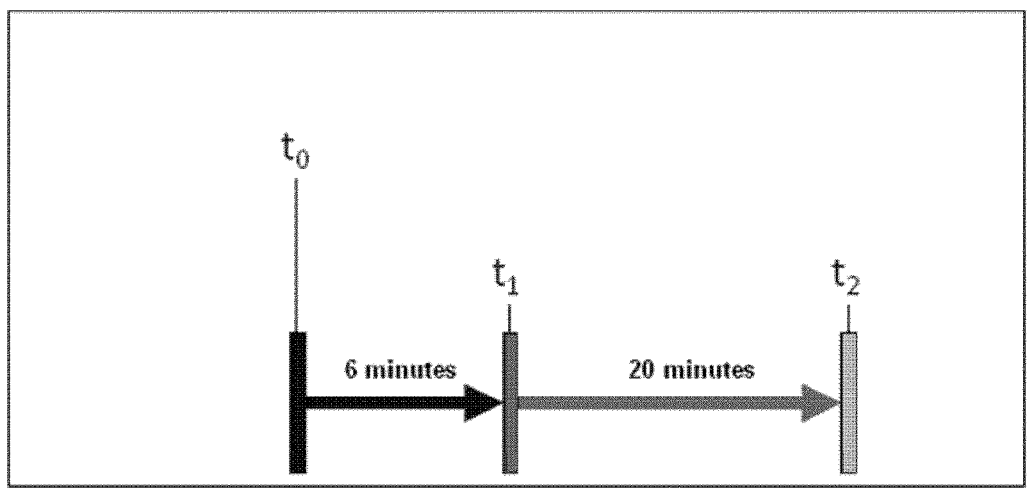
FIG. 3 illustrates the application process of an aqueous emulsion (A) according to the invention as well as a comparative example.

FIG. 3 illustrates the application process of an aqueous emulsion (A) according to the invention as well as a comparative example. 2 ml of aqueous emulsion (A) as described in Table 1 was administered to a test animal 1 at a time $t_0$. At the same time ($t_0$) 2 ml of a sodium chloride solution was administered to a test animal 2, used as a comparative example. After 6 minutes ($t_1$) both test animals received 1.5 ml of aqueous emulsion (B) as described in Table 2. After 20 minutes ($t_2$) both test animals were subjected to an MR-imaging process.

Figure 4:
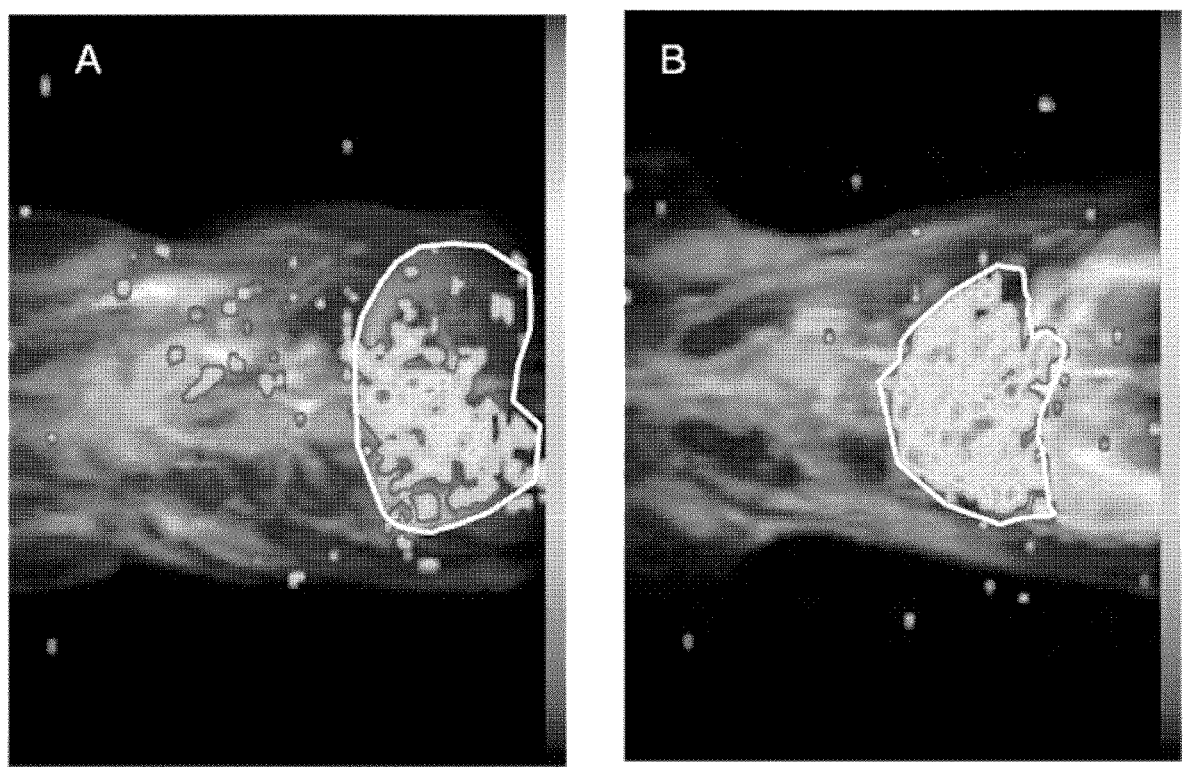
FIG. 4 shows exemplary 3D reconstructions of the anatomic T2-weighted MR images of two test animals which are superimposed with a colored $^{19}$F image wherein the liver is encircled in white after the application process described in FIG. 3.

FIG. 4 shows exemplary 3D reconstructions of the anatomic T2-weighted MR images which are superimposed with a colored $^{19}F$ image wherein the liver is encircled in white. As can be clearly seen by comparison of image (A) and image (B), the accumulation of the contrast agent in the liver of test animal 1 is significantly reduced (image (A)). Thus, it could be demonstrated that the pharmacokinetics of emulsion (B) can be modified by the prior administration of aqueous emulsion (A) in such a way that less of the contrast agent accumulates in the liver and spleen of the test animal.

Figure 5:
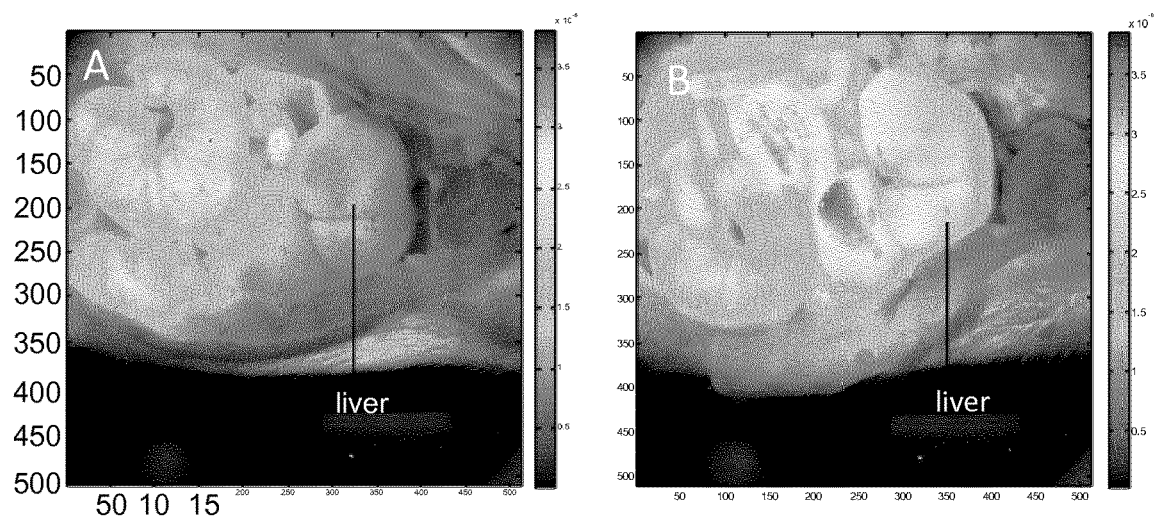
FIG. 5 shows in-situ fluorescence images of two test animals which were treated with aqueous emulsions according to the administration procedure described with respect to FIG. 3.

FIG. 5 shows in-situ fluorescence images of two test animals which were treated according to the administration procedure above. Both animals received 2 ml of emulsion (B) as described in Table 2 which additionally contained a fluorescent dye. Animal 1 also received an aqueous emulsion (A) prior to the administration of the contrast agent while test animal 2 only received a sodium chloride injection. As can be clearly seen the intensity of the fluorescent signal in animal 1 (image A) is significantly reduced in comparison to animal 2 (image B). Thus, it is demonstrated that a pre-saturation of the liver as described in the present invention significantly hinders the accumulation of the fluorinated contrast agent in the liver thus leaving more of the contrast agent available for the macrophages relevant for the visualization of inflamed tissue. In order to better illustrate the different amounts of contrast agent in the liver of the two animals, both livers were removed and imaged ex vivo. The fluorescence intensity, coded in false-colors, is shown in FIG. 6.

Figure 6:
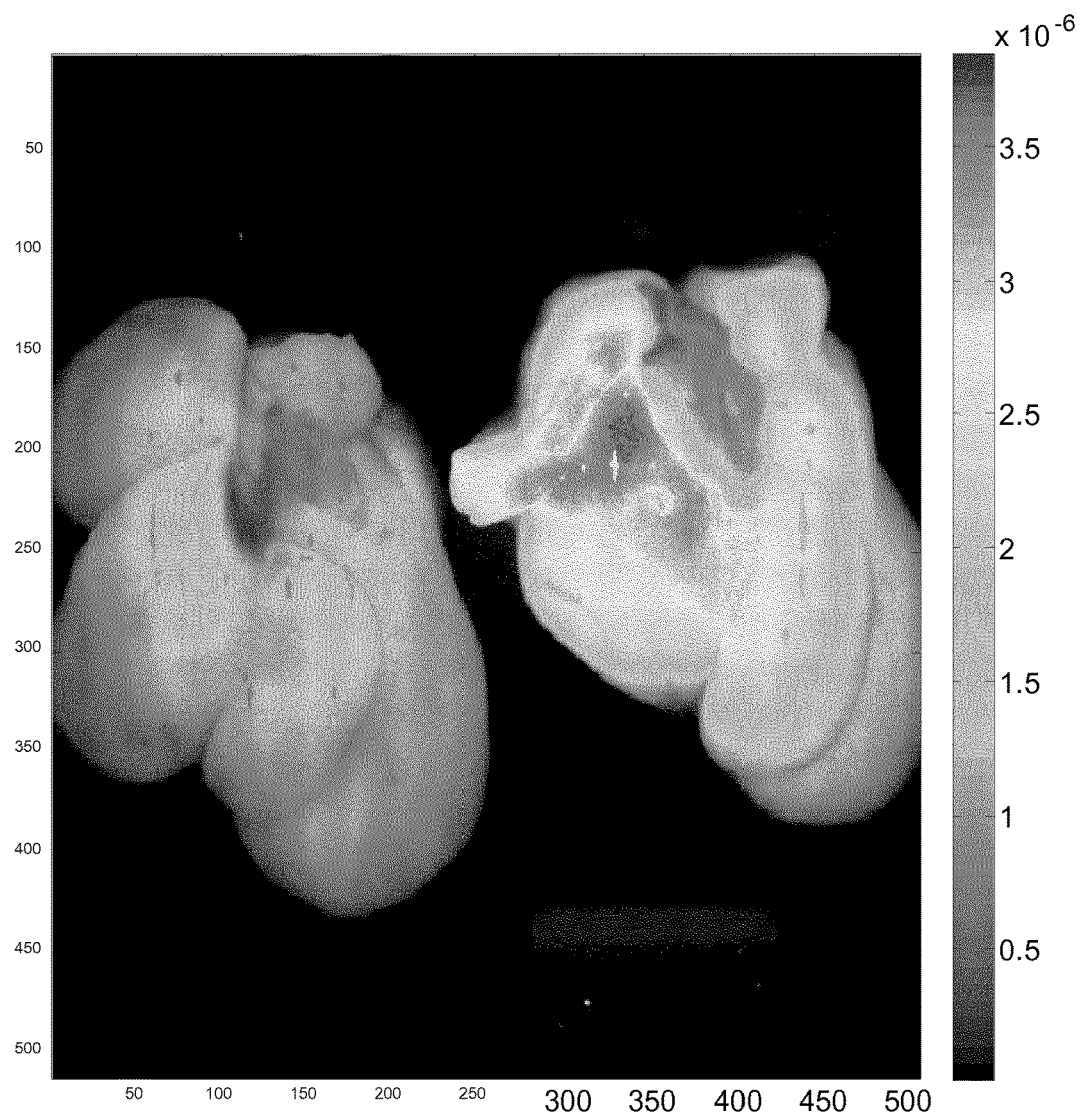
FIG. 6 shows the fluorescent intensity, coded in false colors, of the liver of the two test animals of FIG. 5.

The liver shown on the left-hand side of FIG. 6 was excised from test animal 1 whose liver phagocytic cells were pre-saturated by administration of aqueous emulsion (A). As can be seen, the intensity of the fluorescence signal is rather low compared to the liver on the right-hand side which was taken from test animal 2 which was not injected with an aqueous emulsion (A). The concentration of the contrast agent is much higher, as is revealed by the higher intensity of the fluorescent signal.

Further, the stability of the composition comprising a fluorinated contrast agent as described in the invention, meaning as an emulsion, has been tested. The emulsions tested are shown in Table 4 as well as a comparative example. The amounts given refer to wt.-%, based on the total weight of the emulsion.

TABLE 4

| Component | Example 1 | Example 2 | Example 3 | Example 9 |
|---|---|---|---|---|
| F6H8[1] | 4 | 6 | 8 | 20 |
| MCT[2] | 16 | 14 | 12 | — |
| Lipoid E 80[3] | 2 | 2 | 2 | 2 |
| Water | Ad 100 | Ad 100 | Ad 100 | Ad 100 |

[1] Perfluorohexyloctane ex Novaliq, Germany
[2] Mid chain triglyceride (50-80 wt.-% $C_8$-fatty acid and 20-50 wt.-% $C_{10}$-fatty acid)
[3] egg phospholipid ex Lipoid GmbH, Germany.

The results of the stability tests are shown in Table 5. Average particle diameter (ZAverage) and polydispersity index (P.I.) were determined by photon correlation spectroscopy (PCS).

TABLE 5

Storage stability data of the emulsions according to examples 1 to 3 of Table 4.

| Example | Storage time [days] | ZAverage [nm] | P.I. | pH |
|---|---|---|---|---|
| 1 | 0 | 148.3 | 0.073 | 8.09 |
|   | 7 | 158.1 | 0.093 | 6.61 |
|   | 14 | 169.2 | 0.098 | 6.12 |
|   | 28 | 173.9 | 0.098 | 5.83 |
| 2 | 0 | 166.1 | 0.054 | 8.10 |
|   | 7 | 173.6 | 0.075 | 6.59 |
|   | 14 | 184.2 | 0.061 | 6.19 |
|   | 28 | 185.0 | 0.069 | 5.96 |
| 3 | 0 | 155.7 | 0.075 | 8.11 |
|   | 7 | 167.7 | 0.065 | 6.62 |
|   | 14 | 176.7 | 0.068 | 6.08 |
|   | 28 | 178.5 | 0.090 | 5.98 |

Figure 7:
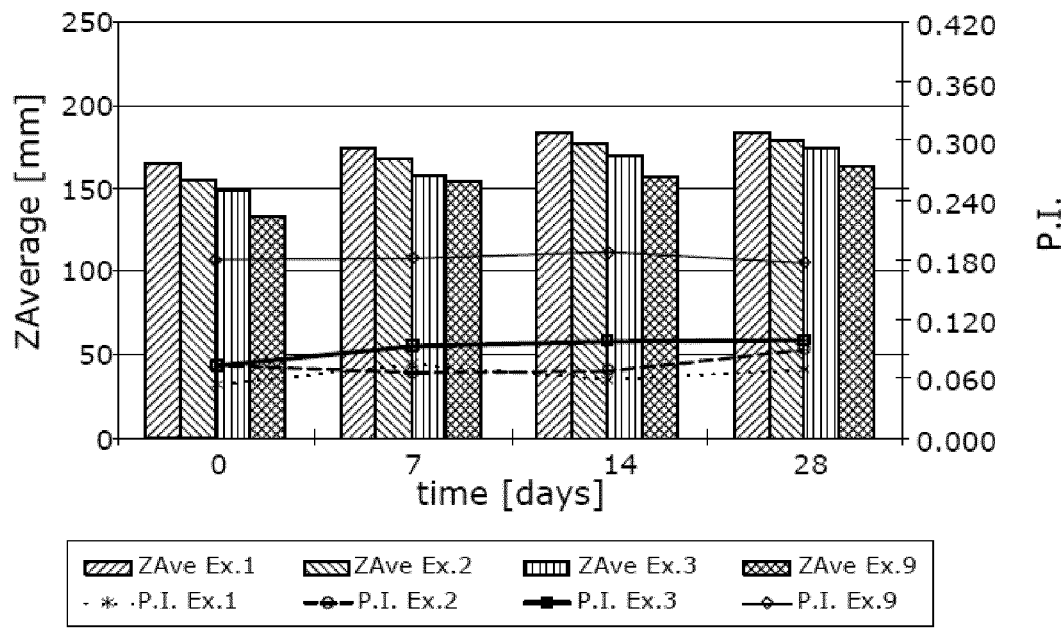
FIG. 7 shows the data of the storage stability tests as reflected in Table 5, as well as the data concerning the comparative example given.

FIG. 7 shows the data of the storage stability tests as reflected in Table 5 as well as the data concerning the comparative example given.

Figure 7A:
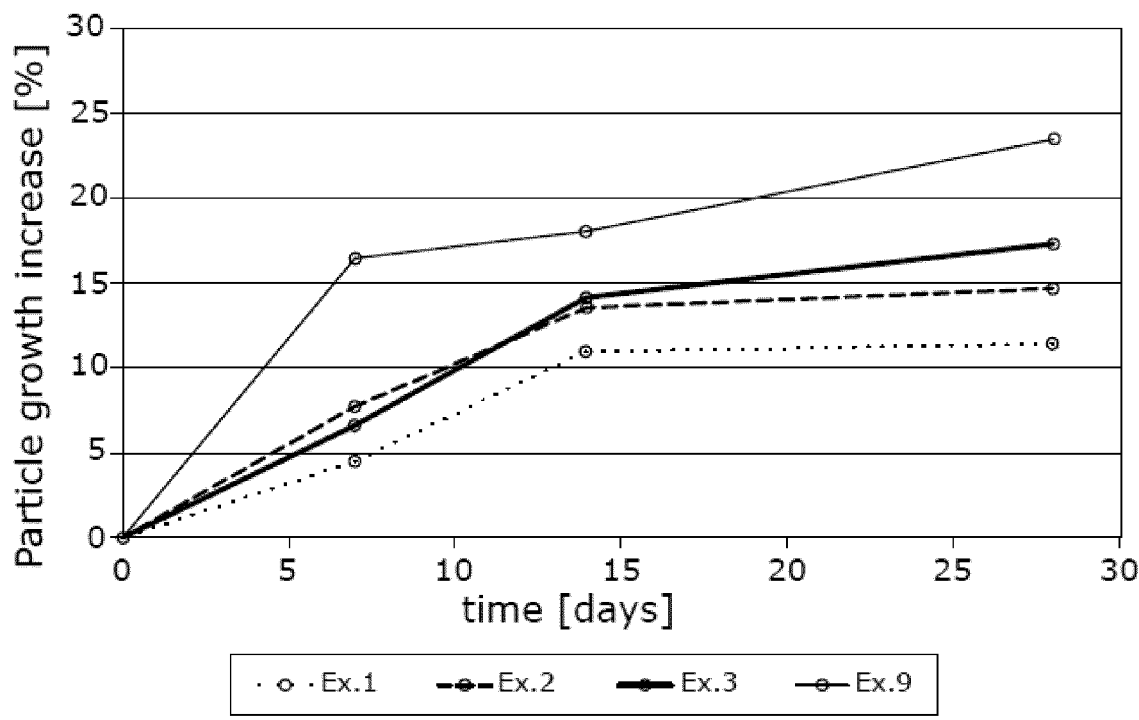
FIG. 7A shows the particle growth of the emulsions according to examples 1 to 3 as well as the comparative example given in Table 4.

FIG. 7A shows the particle growth of the emulsions according to examples 1 to 3 as well as the comparative example given in Table 4. The particle growths measurement started immediately after the manufacturing of the emulsion.

FIG. 7A further shows that the average particle diameter of the oil droplets within 28 days increases by about 11% for example 1, by about 15% for example 2 by about 17% for example 3 and by about 23% for the comparative example. The higher the concentration of the semifluorinated compound the higher the increase in particle growth.

Figure 7B:
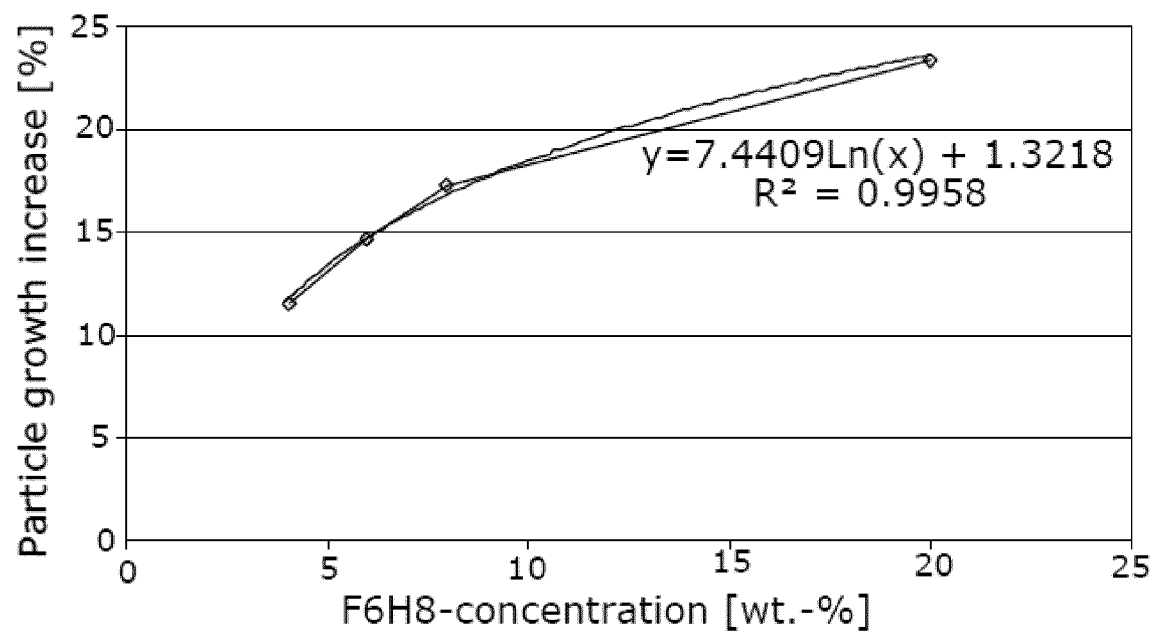
FIG. 7B shows the dependency of the particle growth increase on the concentration of the semifluorinated compound F6H8.

FIG. 7B shows the dependency of the particle growth increase on the concentration of the semifluorinated compound F6H8.

Table 5A reflects the data which are shown in FIGS. 7, 7A and 7B. The storage tests have been carried out at 20° C.

TABLE 5A

| Example | Storage time [days] | ZAverage [nm] | P.I. | Absolute Particle growth increase [nm] | Relative Particle growth increase [%] |
|---|---|---|---|---|---|
| 1 | 0 | 148.3 | 0.073 | 0.0 | 0.0 |
|   | 7 | 158.1 | 0.093 | 7.5 | 4.5 |
|   | 14 | 169.2 | 0.098 | 18.1 | 10.9 |
|   | 28 | 173.9 | 0.098 | 18.9 | 11.4 |
| 2 | 0 | 166.1 | 0.054 | 0.0 | 0.0 |
|   | 7 | 173.6 | 0.075 | 12.0 | 7.7 |
|   | 14 | 184.2 | 0.061 | 21.0 | 13.5 |
|   | 28 | 185.0 | 0.069 | 22.8 | 14.6 |
| 3 | 0 | 155.7 | 0.075 | 0.0 | 0.0 |
|   | 7 | 167.7 | 0.065 | 9.8 | 6.6 |
|   | 14 | 176.7 | 0.068 | 10.9 | 14.1 |
|   | 28 | 178.5 | 0.090 | 25.6 | 17.3 |
| Example 9 | 0 | 132.4 | 0.181 | 0.0 | 0.0 |
|   | 7 | 154.1 | 0.183 | 21.7 | 16.4 |
|   | 14 | 156.2 | 0.187 | 23.8 | 18.0 |
|   | 28 | 163.4 | 0.177 | 31.0 | 23.4 |

It has been found that an optimized balance of a high concentration of the semifluorinated compound (which is necessary to achieve a good contrast in the MR measurement) and a storage stable emulsion can be achieved if the density of the oil droplets (MCT and semifluorinated compound) is approximately the same as the density of the aqueous phase. By adapting the density of the oil phase to the density of the aqueous phase coalescence phenomena of the droplets as well as sedimentation phenomena, which destabilize the emulsion, can be decreased.

Figure 7C:
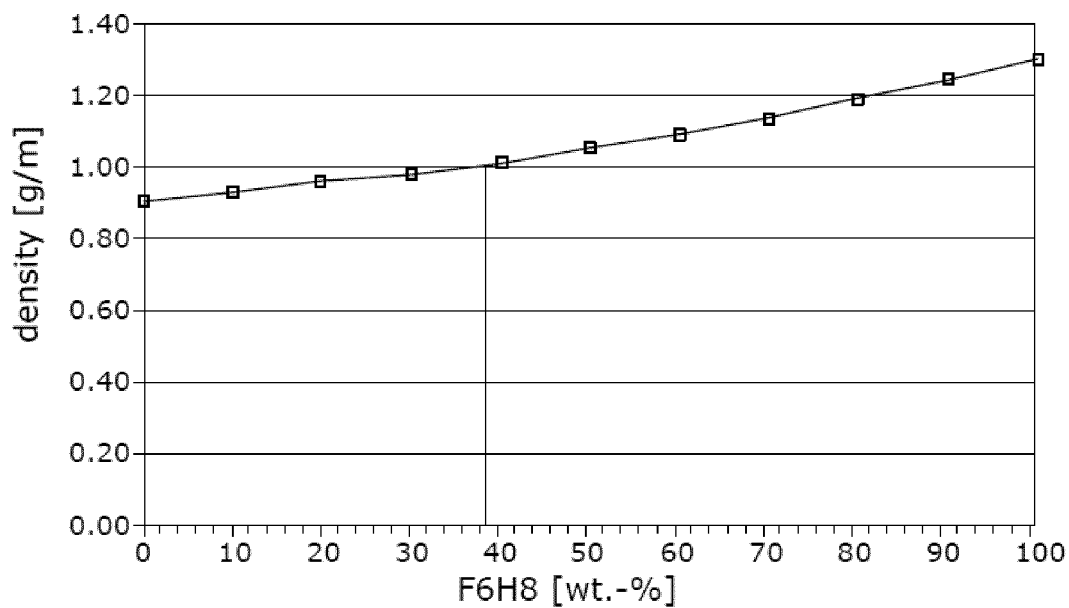
FIG. 7C shows the results of the density measurement of different mixtures of MCT and F6H8.

FIG. 7C shows the results of the density measurement of different mixtures of MCT and F6H8.

At about 38.5 wt.-% of F6H8 and about 61.5 wt.-% of MCT, (weight based on the total weight of the oil phase) the density of the oil mixture corresponds to the density of the aqueous phase.

EXAMPLES 1A-8A, 9A AND 10-12

Perfluoroctylbromide (PFOB) is a known contrast agent for the magnetic resonance spectroscopy. It has been found that PFOB cannot be dissolved in MCT. Therefore, emulsions have been prepared wherein the PFOB is stabilized by perfluorodecylbromide (PFDB) which can be dissolved in PFOB.

Table 6, Table 7, and Table 8 show the oil in water emulsion compositions of examples 1A-8A, 9A and 10-12 and Table 9 shows the respective storage stability data at 20° C. The amounts referred to in Tables 4 and 5 are weight-% (wt.-%) based on the total weight of the emulsion.

TABLE 6

| Examples 1A to 4A | | | | |
|---|---|---|---|---|
| Component | Example 1A | Example 2A | Example 3A | Example 4A |
| PFOB[1] | 20 | 20 | 20 | 20 |
| PFDB[2] | 0.2 | 1 | 2 | 4 |
| Lipoid E 80[3] | 2 | 2 | 2 | 2 |
| Water | Ad 100 | Ad 100 | Ad 100 | Ad 100 |

[1]Perfluoroctylbromide ex ABCR GmbH & Co. KG, Germany
[2]Perfluordecylbromide ex ABCR GmbH & Co. KG, Germany
[3]Egg phospholipid ex Lipoid GmbH, Germany

TABLE 7

| Examples 5A to 8A | | | | |
|---|---|---|---|---|
| Component | Example 5A | Example 6A | Example 7A | Example 8A |
| PFOB[1] | 20 | 20 | 20 | 20 |
| PFDB[2] | 0.2 | 1 | 2 | 4 |
| Lipoid S PC-3[3] | 2 | 2 | 2 | 2 |
| Water | Ad 100 | Ad 100 | Ad 100 | Ad 100 |

[1]Perfluoroctylbromide
[2]Perfluordecylbromide
[3]Phospholipid ex Lipoid GmbH, Germany

TABLE 8

| Examples 9A and 10 to 12 | | | | |
|---|---|---|---|---|
| Component | Example 9A | Example 10A | Example 11A | Example 12A |
| PFOB[1] | 20 | 20 | 20 | 20 |
| PFDB[2] | 0.2 | 1 | 2 | 4 |
| Lipoid S 75[3] | 2 | 2 | 2 | 2 |
| Water | Ad 100 | Ad 100 | Ad 100 | Ad 100 |

[1]Perfluoroctylbromide ex ABCR GmbH & Co. KG, Germany
[2]Perfluordecylbromide ex ABCR GmbH & Co. KG, Germany
[3]Soja phospholipid ex Lipoid GmbH, Germany

TABLE 9

Storage stability data of the emulsions according to examples 1A to 12A

| Example | Storage time [days] | ZAverage [nm] | P.I. | pH |
|---|---|---|---|---|
| 1A | 0 | 168.5 | 0.128 | 6.93 |
|    | 7 | 314.3 | 0.197 | 5.59 |
|    | 14 | 310.0 | 0.217 | 5.14 |
|    | 28 | 316.5 | 0.242 | 4.52 |
| 2A | 0 | 119.7 | 0.187 | 6.75 |
|    | 7 | 270.8 | 0.150 | 5.55 |
|    | 14 | 278.4 | 0.221 | 5.35 |
|    | 28 | 267.6 | 0.187 | 5.32 |
| 3A | 0 | 157.7 | 0.155 | 7.11 |
|    | 7 | 249.0 | 0.156 | 5.85 |
|    | 14 | 263.7 | 0.153 | 5.53 |
|    | 28 | 178.4 | 0.061 | 5.74 |
| 4A | 0 | 157.5 | 0.193 | 6.99 |
|    | 7 | 244.7 | 0.121 | 6.01 |
|    | 14 | 267.5 | 0.120 | 5.71 |
|    | 28 | 259.2 | 0.154 | 5.55 |

TABLE 9-continued

Storage stability data of the emulsions according to examples 1A to 12A

| Example | Storage time [days] | ZAverage [nm] | P.I. | pH |
|---|---|---|---|---|
| 5A | 0 | 141.5 | 0.222 | 7.25 |
|  | 7 | 318.8 | 0.160 | 6.47 |
|  | 14 | 377.9 | 0.250 | 6.40 |
|  | 28 | 485.8 | 0.358 | 6.04 |
| 6A | 0 | 130.1 | 0.282 | 7.27 |
|  | 7 | 290.5 | 0.134 | 6.98 |
|  | 14 | 444.3 | 0.224 | 6.62 |
|  | 28 | 365.5 | 0.257 | 6.73 |
| 7A | 0 | 146.7 | 0.184 | 7.75 |
|  | 7 | 269.0 | 0.171 | 6.96 |
|  | 14 | 289.8 | 0.160 | 5.83 |
|  | 28 | 315.4 | 0.156 | 6.56 |
| 8A | 0 | 141.9 | 0.217 | 7.58 |
|  | 7 | 230.8 | 0.129 | 6.68 |
|  | 14 | 253.0 | 0.117 | 6.69 |
|  | 28 | 346.6 | 0.133 | 5.90 |
| 9A | 0 | 170.1 | 0.117 | 7.29 |
|  | 7 | 272.8 | 0.114 | 6.38 |
|  | 14 | 283.2 | 0.121 | 5.79 |
|  | 28 | 249.6 | 0.071 | 5.23 |
| 10A | 0 | 152.4 | 0.137 | 7.18 |
|  | 7 | 241.8 | 0.094 | 5.96 |
|  | 14 | 233.5 | 0.100 | 5.59 |
|  | 28 | 243.3 | 0.092 | 5.29 |
| 11A | 0 | 165.5 | 0.128 | 7.18 |
|  | 7 | 217.5 | 0.115 | 6.04 |
|  | 14 | 224.1 | 0.136 | 6.03 |
|  | 28 | 224.8 | 0.096 | 5.66 |
| 12A | 0 | 144.9 | 0.135 | 7.24 |
|  | 7 | 207.0 | 0.127 | 5.78 |
|  | 14 | 212.4 | 0.092 | 5.97 |
|  | 28 | 208.9 | 0.107 | 5.71 |

Figure 8:
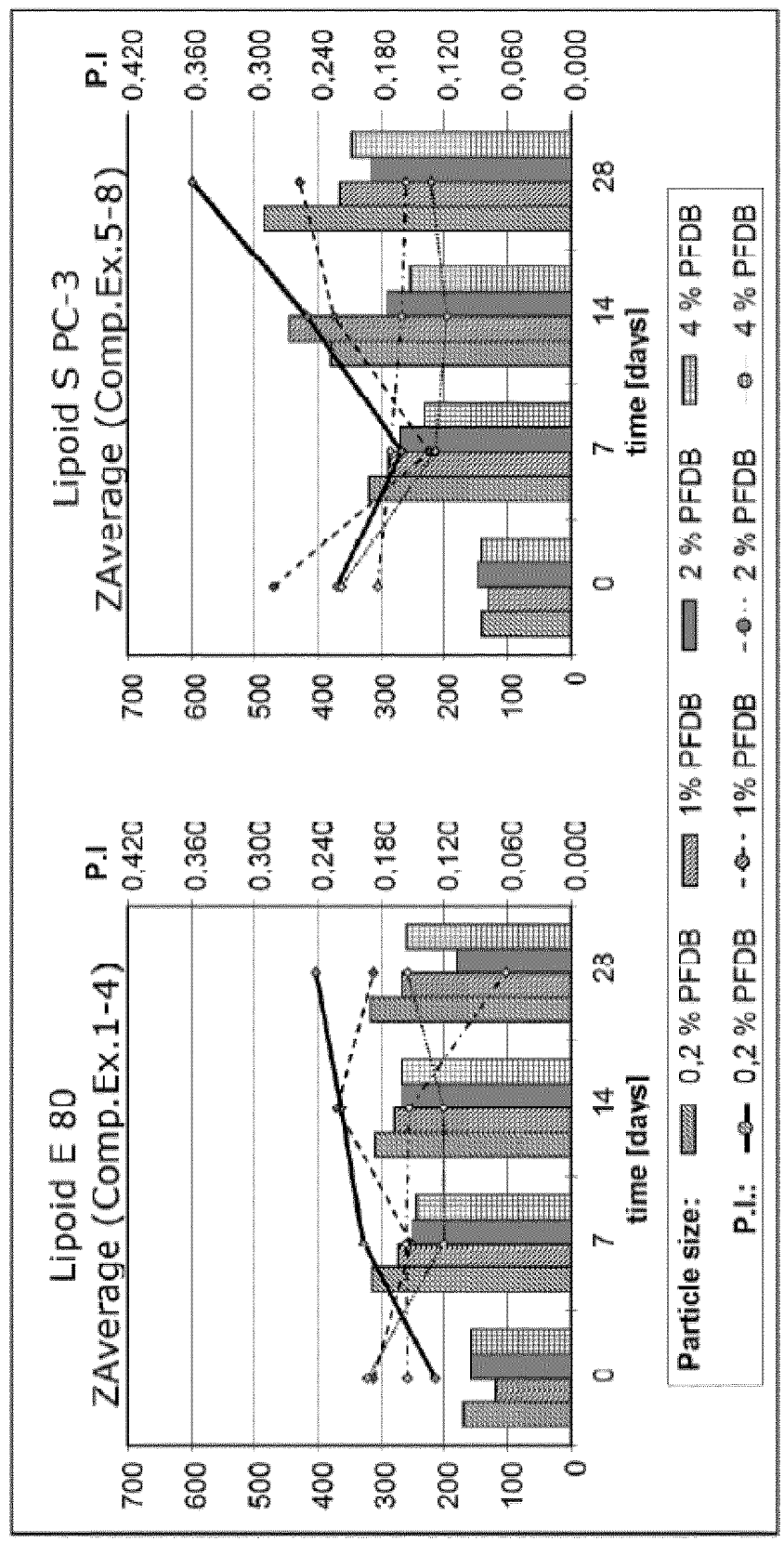
FIG. 8 shows the data for the storage stability tests as reflected in Table 9 for examples 1A to 4A and 5A to 8A.
Figure 8A:
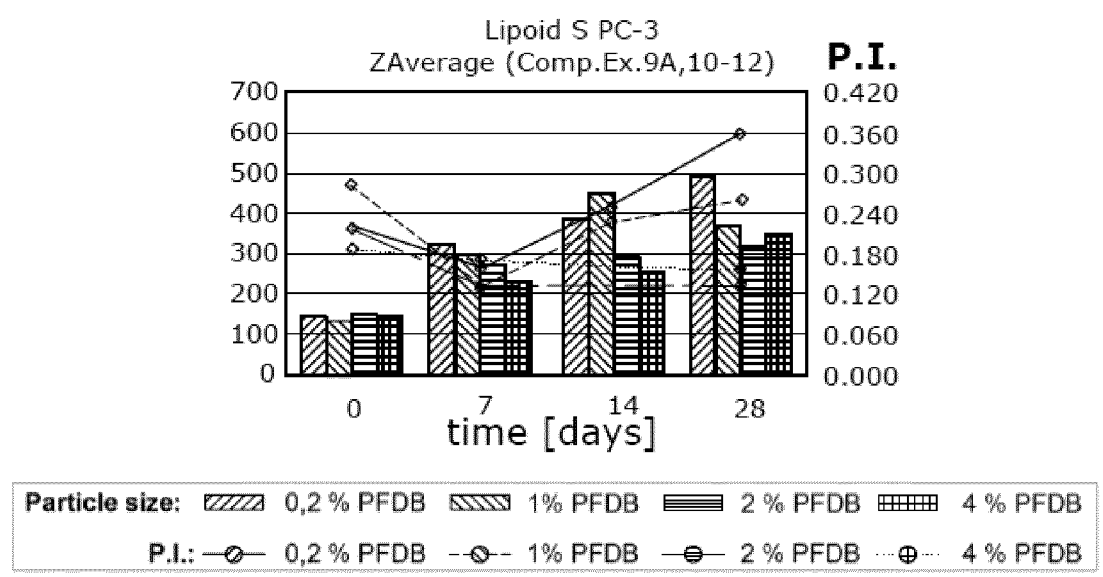
FIG. 8A shows the data for the storage stability tests as reflected in Table 9 for examples 9A and 10-12.

FIG. 8 and FIG. 8A show the data for the storage stability tests as reflected in Table 9. In the left part of FIG. 8 the data for the emulsions according to examples 1A to 4A and in the right part the data for the emulsions according to examples 5A to 8A are depicted. FIG. 8A shows the data for the emulsions according to examples 9A and 10-12.

Test with Different Emulsifier

It has been surprisingly found that the emulsions of the present invention can be further stabilized by the selection of the emulsifier.

The emulsifier Lipid S PC-3 is considered less suitable (FIG. 8) and has not been further tested for the emulsions of the invention.

Table 10 shows emulsions of the present invention according to examples 4 and 5.

TABLE 10

Oil-in-water emulsions according to examples 4 and 5

| Component | Example 4 | Example 5 |
|---|---|---|
| F6H8[1] | 8 | 8 |
| MCT[2] | 12 | 12 |
| Lipoid E 80[3] | 2 | — |
| Lipoid S 75[4] | — | 2 |
| Sodium oleate | 0.03 | 0.03 |
| alpha-tocopherol | 0.02 | 0.02 |
| Water | Ad 100 | Ad 100 |

[1] Perfluorhexyloctane ex Novaliq, Germany
[2] Mid chain triglycerides (50-80 wt.-% $C_8$-fatty acid; 20-50 wt.-% $C_{10}$-fatty acid)
[3] Egg Phospholipid ex Lipoid GmbH, Germany
[4] Phospholipid ex Lipoid GmbH, Germany (soya phospholipid with 14 to 25 wt.-% glycolipid)

The emulsions according to example 4 and example 5 are further analysed whether sterilization conditions effect the stability of the emulsions. The emulsions have been sterilized in a rotating autoclave and are compared with not sterilized emulsions (sterilization condition: heating at 121° C. for 15 min at 2 bar).

Table 11 shows the stability data of the emulsions according to example 4 and 5 without sterilization and after sterilization.

TABLE 11

Storage stability data for examples 4 and 5 of the invention under sterilized and not sterilized conditions

| Example | Sterilized/ Not sterilized | Storage time [days] | ZAverage [nm] | P.I. | pH |
|---|---|---|---|---|---|
| 4 | Not sterilized | 0 | 156.5 | 0.082 | 8.13 |
|  |  | 7 | 170.5 | 0.108 | 5.84 |
|  |  | 14 | 176.6 | 0.086 | 5.68 |
|  |  | 28 | 194.9 | 0.043 | 5.00 |
|  | sterilized | 0 | 156.5 | 0.082 | 8.13 |
|  |  | 7 | 263.2 | 0.028 | 7.15 |
|  |  | 14 | 264.9 | 0.072 | 7.12 |
|  |  | 28 | 260.8 | 0.040 | 7.07 |
| 5 | Not sterilized | 0 | 170.6 | 0.102 | 8.00 |
|  |  | 7 | 176.9 | 0.080 | 6.40 |
|  |  | 14 | 177.7 | 0.075 | 5.12 |
|  |  | 28 | 167.0 | 0.067 | 4.07 |
|  | sterilized | 0 | 170.6 | 0.102 | 8.00 |
|  |  | 7 | 177.0 | 0.059 | 8.09 |
|  |  | 14 | 178.9 | 0.095 | 8.00 |
|  |  | 28 | 175.4 | 0.086 | 7.93 |

Figure 9:
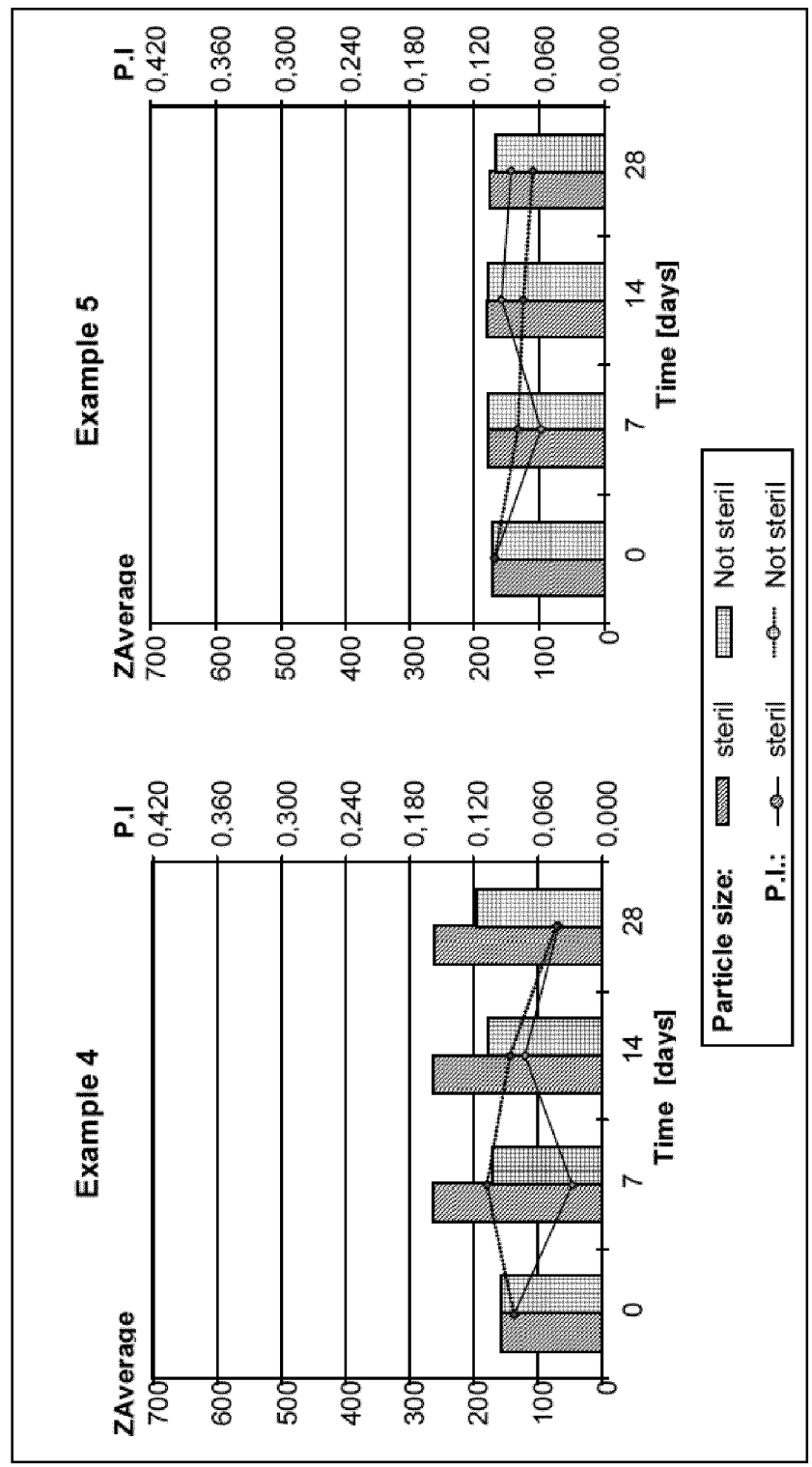
FIG. 9 shows the data for the storage stability tests as reflected in Table 11.

FIG. 9 shows the data for the storage stability tests as reflected in Table 11. In the left part of FIG. 9 the data for the emulsions according to example 4 and in the right part the data for the emulsions according to example 5 are depicted.

FIG. 9 and Table 11 show that the emulsion according to example 5 is more stable than the emulsion of example 4. The emulsion according to example 5 is also more stable after the emulsion has been sterilized in a rotating autoclave.

Further the emulsions of example 4 and 5 have been stored for 168 days at 40° C.

Figure 9A:
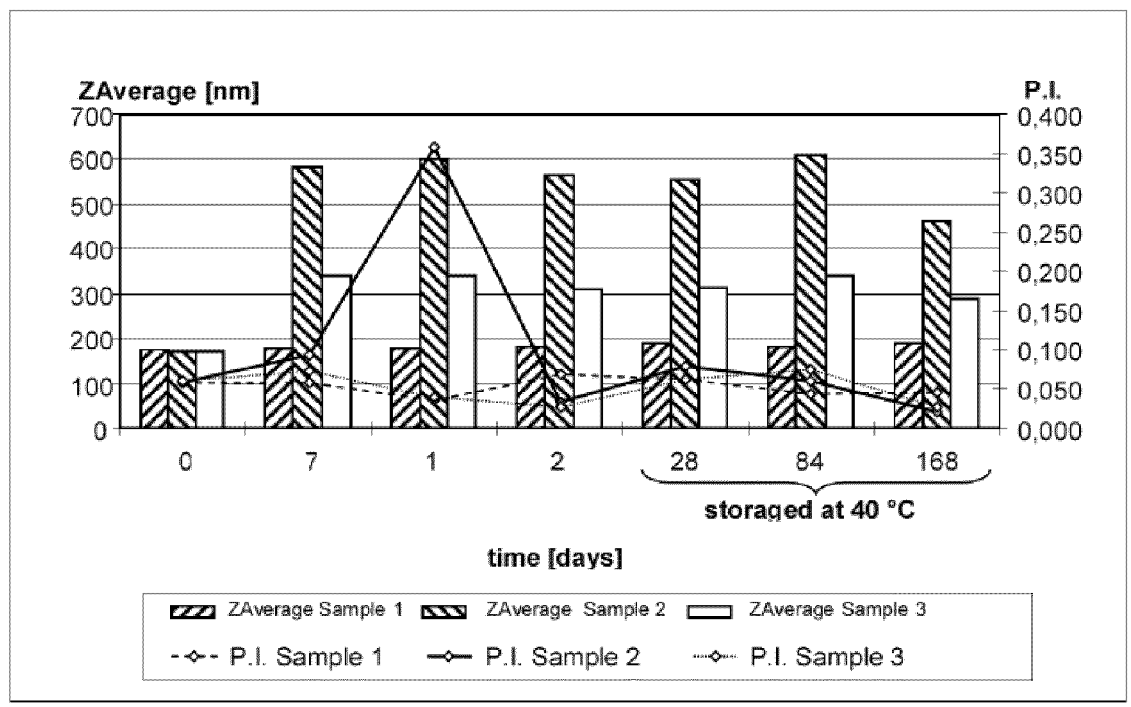
FIG. 9A shows the test results of 3 samples of the emulsion according to example 4.

FIG. 9A shows the test results of 3 samples of the emulsion according to example 4.

Figure 10:
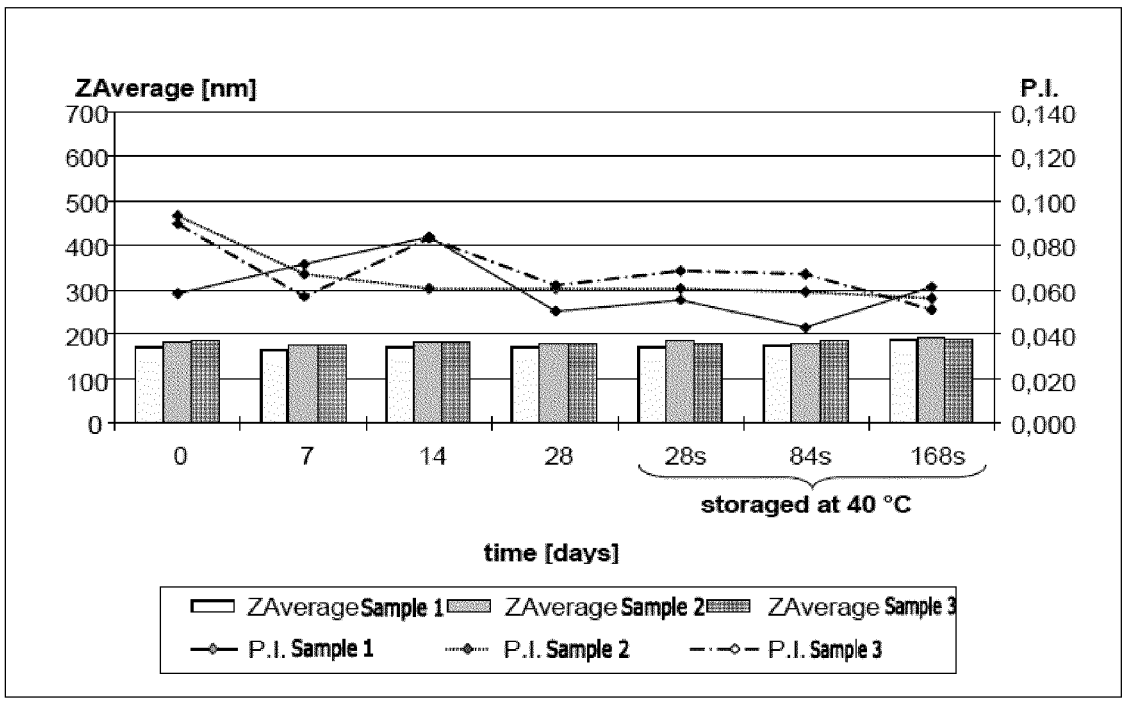
FIG. 10 shows the test results of 3 samples of the emulsion according to example 5.

FIG. 10 shows the test results of 3 samples of the emulsion according to example 5. It has surprisingly found that the emulsion of example 5 even at a storage temperature of 40° C. did not significantly change the physical stability (FIG. 10).

The invention claimed is:

1. A method for diagnostic detection of pathological conditions, the method comprising:
    (a) parenterally administering a phagocytosable-component-containing oil-in-water emulsion to a patient, wherein the oil-in-water emulsion comprises an oil present in an amount ranging from 5 to 40 wt.-% based on the total weight of the oil-in-water emulsion, wherein the oil comprises a long chain triglyceride;
    (b) administering a composition comprising a fluorinated contrast agent and a medium chain triglyceride to the patient; and
    (c) acquiring one or more non-invasive images of the patient, wherein the one or more non-invasive images are acquired by a magnetic resonance imaging procedure.

2. The method according to claim 1, wherein the time difference between parenterally administering the phagocytosable-component-containing oil-in-water emulsion to the patient and administering the composition comprising the fluorinated contrast a ent and the medium chain triglyceride to the patient is at least 15 seconds.

3. The method according to claim 2, wherein the time difference is at least 30 seconds.

4. The method according to claim 2, wherein the time difference ranges from 1 minute to 10 hours.

5. The method according to claim 1, wherein the time difference ranges from 5 minutes to 1 hour.

6. The method according to claim 1, wherein the oil-in-water emulsion further comprises one or more oils selected from the group consisting of medium-chain triglycerides (MCT) and fish oil.

7. The method according to claim 1, wherein the oil-in-water emulsion further comprises:
   i) 0.5 to 5 wt.-% of an emulsifier,
   ii) optionally 0.1 to 5 wt.-% of a tonicity agent, and
   iii) 55 to 93 wt.-% of water, wherein the wt.-% are based on the total weight of the oil-in-water emulsion, and the composition comprising the fluorinated contrast agent and the medium chain triglyceride is in the form of an aqueous emulsion comprising:
   i) 1 to 20 wt.-% of a semifluorinated compound of formula I:

$$CF_3-(CF_2)_x-(CH_2)_y-CH_3 \qquad (I)$$

wherein x is an integer ranging from 1 to 8 and y is an integer ranging from 2 to 10,
   ii) 1 to 20 wt.-% of the medium chain triglyceride, wherein the medium chain triglyceride is miscible with the semifluorinated compound at 20° C., and
   iii) 0.1 to 5 wt.-% of an emulsifier, wherein the wt.-% are based on the total weight of aqueous emulsion.

8. A kit comprising
   a) a container comprising a phagocytosable-component-containing oil-in-water emulsion, wherein the phagocytosable-component-containing oil-in-water emulsion is a parenteral formulation, wherein the oil-in-water emulsion comprises an oil present in an amount ranging from 5 to 40 wt.-% based on the total weight of the oil-in-water emulsion, wherein the oil comprises a long chain triglyceride, and
   b) a container comprising a composition comprising a fluorinated contrast agent and a medium chain triglyceride, wherein the fluorinated contrast agent is selected from the group consisting of partially fluorinated carbon compounds, perfluorinated carbon compounds, linear, cyclic or polycyclic fluorinated alkanes, bis(perfluoroalkyl)alkenes, perfluoroethers, perfluoroamines, perfluoroalkyl bromide, and perfluoroalkyl chloride.

9. The kit of claim 8, wherein the kit is a diagnostic kit.

10. The kit of claim 8, wherein the oil-in-water emulsion further comprises one or more medium-chain triglycerides (MCT).

11. The kit of claim 8, wherein the oil is present in an amount ranging from 8 to 30 wt.-% based on the total weight of the oil-in-water emulsion.

12. The kit of claim 8, wherein the composition comprising the fluorinated contrast agent and the medium chain triglyceride is an aqueous emulsion comprising:
   a) a semifluorinated compound of formula I:

$$CF_3-(CF_2)_x-(CH_2)_y-CH_3 \qquad (I)$$

wherein x is an integer ranging from 1 to 8 and y is an integer ranging from 2 to 10,
   b) a medium-chain triglyceride (MCT) which is miscible with the semifluorinated compound at 20° C., and
   c) an emulsifier.

13. The kit of claim 8, wherein the phagocytosable-component-containing oil-in-water emulsion facilitates diagnostic detection of inflammatory processes in an imaging procedure.

14. The kit of claim 13, wherein the oil-in-water emulsion further comprises:
   i) 0.5 to 5 wt.-% of an emulsifier,
   ii) optionally 0.1 to 5 wt.-% of a tonicity agent, and
   iii) 55 to 93 wt.-% of water, wherein the wt.-% are based on the total weight of the oil-in-water emulsion, and the composition comprising the fluorinated contrast agent and the medium chain triglyceride is in the form of an aqueous emulsion comprising:
   i) 1 to 20 wt.-% of a semifluorinated compound of formula I:

$$CF_3-(CF_2)_x-(CH_2)_y-CH_3 \qquad (I)$$

wherein x is an integer ranging from 1 to 8 and y is an integer ranging from 2 to 10,
   ii) 1 to 20 wt.-% of the medium chain triglyceride, wherein the medium chain triglyceride is miscible with the semifluorinated compound at 20° C., and
   iii) 0.1 to 5 wt.-% of an emulsifier, wherein the wt.-% are based on the total weight of aqueous emulsion.

15. The kit of claim 14, wherein the emulsifier in the oil-in-water emulsion is a phospholipid.

16. The kit of claim 13, wherein the inflammatory processes are selected from the group consisting of inflammatory reactions associated with myocardial infarction, stroke, myocarditis, encephalitis, meningitis, multiple sclerosis, Crohn's disease, arteriosclerosis, abscesses, and arthritis, wherein the imaging procedure is based on measuring the nuclear magnetic resonance of a $^{19}F$ isotope.

17. The kit of claim 13, wherein the inflammatory processes are associated with myocardial infarction, myocarditis, atherosclerosis, thrombosis, stroke, tumor, thrombosis, sarcoidosis, inflammatory bowel diseases, and autoimmune diseases.

\* \* \* \* \*